United States Patent
Manzo

(10) Patent No.: US 8,105,320 B2
(45) Date of Patent: Jan. 31, 2012

(54) METHODS FOR REPLACEABLE END-EFFECTOR CARTRIDGES

(75) Inventor: Scott E. Manzo, Shelton, CT (US)

(73) Assignee: Intuitive Surgical Operations Inc., Sunnyvale, CA (US)

( * ) Notice: Subject to any disclaimer, the term of this patent is extended or adjusted under 35 U.S.C. 154(b) by 0 days.

(21) Appl. No.: 12/753,201

(22) Filed: Apr. 2, 2010

(65) Prior Publication Data

US 2010/0198231 A1 Aug. 5, 2010

Related U.S. Application Data

(60) Division of application No. 11/238,794, filed on Sep. 28, 2005, which is a continuation-in-part of application No. 10/126,451, filed on Apr. 18, 2002, now Pat. No. 6,994,708, and a continuation-in-part of application No. 10/611,411, filed on Jun. 30, 2003, now Pat. No. 7,367,973.

(60) Provisional application No. 60/617,341, filed on Oct. 8, 2004.

(51) Int. Cl.
*A61B 17/00* (2006.01)

(52) U.S. Cl. .............................. 606/1; 901/14

(58) Field of Classification Search ................ 606/1, 41, 606/130
See application file for complete search history.

(56) References Cited

U.S. PATENT DOCUMENTS

| | | |
|---|---|---|
| 3,762,019 A | 10/1973 | Epstein |
| 4,281,447 A | 8/1981 | Miller et al. |
| 4,332,066 A | 6/1982 | Hailey et al. |
| 4,360,245 A | 11/1982 | Nikitas |
| 4,486,928 A | 12/1984 | Tucker et al. |
| 4,500,065 A | 2/1985 | Hennekes et al. |
| 4,512,709 A | 4/1985 | Hennekes et al. |
| 4,706,372 A | 11/1987 | Ferrero et al. |
| 4,710,093 A | 12/1987 | Zimmer et al. |
| 4,793,053 A | 12/1988 | Zuccaro et al. |
| 4,809,747 A | 3/1989 | Choly et al. |
| 4,830,569 A | 5/1989 | Jannborg |
| 5,018,266 A | 5/1991 | Hutchinson et al. |
| 5,174,300 A | 12/1992 | Bales et al. |
| 5,184,601 A | 2/1993 | Putman |
| 5,294,209 A | 3/1994 | Naka et al. |

(Continued)

FOREIGN PATENT DOCUMENTS

WO WO-9950721 10/1999

OTHER PUBLICATIONS

U.S. Appl. No. 09/399,457, filed Sep. 17, 1999 (now abandoned), Ramans, Andris D.

(Continued)

*Primary Examiner* — Michael Peffley
*Assistant Examiner* — Samantha Good

(57) ABSTRACT

In one embodiment of the invention, a replaceable electrosurgical end effector cartridge is provided to couple to a mechanical wrist of a surgical instrument for a robotic surgical system. The replaceable electrosurgical end effector cartridge includes two end effectors, a fastener to rotatably couple the two end effectors together, and a cam mechanism. At least one of the two end effectors is a moveable end effector having a jaw portion, an off-center portion, and a base portion. The cam mechanism is coupled to the base portion of the at least one moveable end effector to pivot it about the fastener to open and close the jaw portion of the at least one moveable end effector with respect to the other.

8 Claims, 19 Drawing Sheets

U.S. PATENT DOCUMENTS

| | | | |
|---|---|---|---|
| 5,313,935 A | 5/1994 | Kortenbach et al. |
| 5,372,147 A | 12/1994 | Lathrop, Jr. et al. |
| 5,429,596 A | 7/1995 | Arias et al. |
| 5,445,166 A | 8/1995 | Taylor |
| 5,507,297 A | 4/1996 | Slater et al. |
| 5,620,459 A | 4/1997 | Lichtman |
| 5,649,956 A | 7/1997 | Jensen et al. |
| 5,792,135 A | 8/1998 | Madhani et al. |
| 5,797,900 A | 8/1998 | Madhani et al. |
| 5,800,423 A | 9/1998 | Jensen |
| 5,807,378 A | 9/1998 | Jensen et al. |
| 5,808,665 A | 9/1998 | Green |
| 5,855,583 A | 1/1999 | Wang et al. |
| 5,976,122 A | 11/1999 | Madhani et al. |
| 6,004,509 A | 12/1999 | Dey et al. |
| 6,006,633 A | 12/1999 | Kaiser et al. |
| 6,083,222 A | 7/2000 | Klein et al. |
| 6,102,909 A | 8/2000 | Chen et al. |
| 6,108,845 A | 8/2000 | Hung et al. |
| 6,113,596 A | 9/2000 | Hooven et al. |
| 6,132,368 A | 10/2000 | Cooper |
| 6,132,441 A | 10/2000 | Grace |
| 6,152,923 A | 11/2000 | Ryan |
| 6,162,220 A | 12/2000 | Nezhat |
| 6,206,903 B1 | 3/2001 | Ramans |
| 6,246,200 B1 | 6/2001 | Blumenkranz et al. |
| 6,309,397 B1 | 10/2001 | Julian et al. |
| 6,312,435 B1 | 11/2001 | Wallace et al. |
| 6,331,181 B1 | 12/2001 | Tierney et al. |
| 6,364,888 B1 | 4/2002 | Niemeyer et al. |
| 6,424,885 B1 | 7/2002 | Niemeyer et al. |
| 6,436,107 B1 | 8/2002 | Wang et al. |
| 6,458,130 B1 | 10/2002 | Frazier et al. |
| 6,464,701 B1 | 10/2002 | Hooven et al. |
| 6,491,691 B1 | 12/2002 | Morley et al. |
| 6,511,480 B1 | 1/2003 | Tetzlaff et al. |
| 6,676,669 B2 | 1/2004 | Charles et al. |
| 6,702,805 B1 | 3/2004 | Stuart |
| 6,714,839 B2 | 3/2004 | Salisbury, Jr. et al. |
| 6,720,988 B1 | 4/2004 | Gere et al. |
| 6,746,443 B1 | 6/2004 | Morley et al. |
| 6,758,843 B2 | 7/2004 | Jensen |
| 6,783,524 B2 | 8/2004 | Anderson et al. |
| 6,788,018 B1 | 9/2004 | Blumenkranz |
| 6,817,974 B2 | 11/2004 | Cooper et al. |
| 6,840,938 B1 | 1/2005 | Morley et al. |
| 6,994,708 B2 | 2/2006 | Manzo |
| 7,121,781 B2 | 10/2006 | Sanchez |
| 7,367,973 B2 | 5/2008 | Manzo et al. |
| 2006/0074406 A1 | 4/2006 | Cooper et al. |
| 2006/0167440 A1 | 7/2006 | Cooper et al. |

OTHER PUBLICATIONS

U.S. Appl. No. 60/111,713, filed Dec. 8, 1998, Younge, Robert G.
U.S. Appl. No. 60/617,341, filed Oct. 8, 2004, Manzo, Scott et al.
U.S. Appl. No. 60/111,711, filed Dec. 8, 1998, Neimeyer, Gunter.
U.S. Appl. No. 601431,636, filed Dec. 6, 2002, Cooper, Thomas G. et al.
U.S. Appl. No. 60/285,485, filed Apr. 19, 2001, Anderson, Stephen C.
U.S. Appl. No. 11/238,794 Final Office Action mailed Dec. 4, 2009, 15 pages.
U.S. Appl. No. 11/238,794 Office Action mailed May 4, 2009, 14 pages.
Vertut, Jean et al., "Robot Technology: Teleoperation and Robotics Evolution and Development—vol. 3A", English translation Prentice-Hall, Inc., Inglewood Cliffs, NJ, USA 1986, vol. 3A, 332 pages.

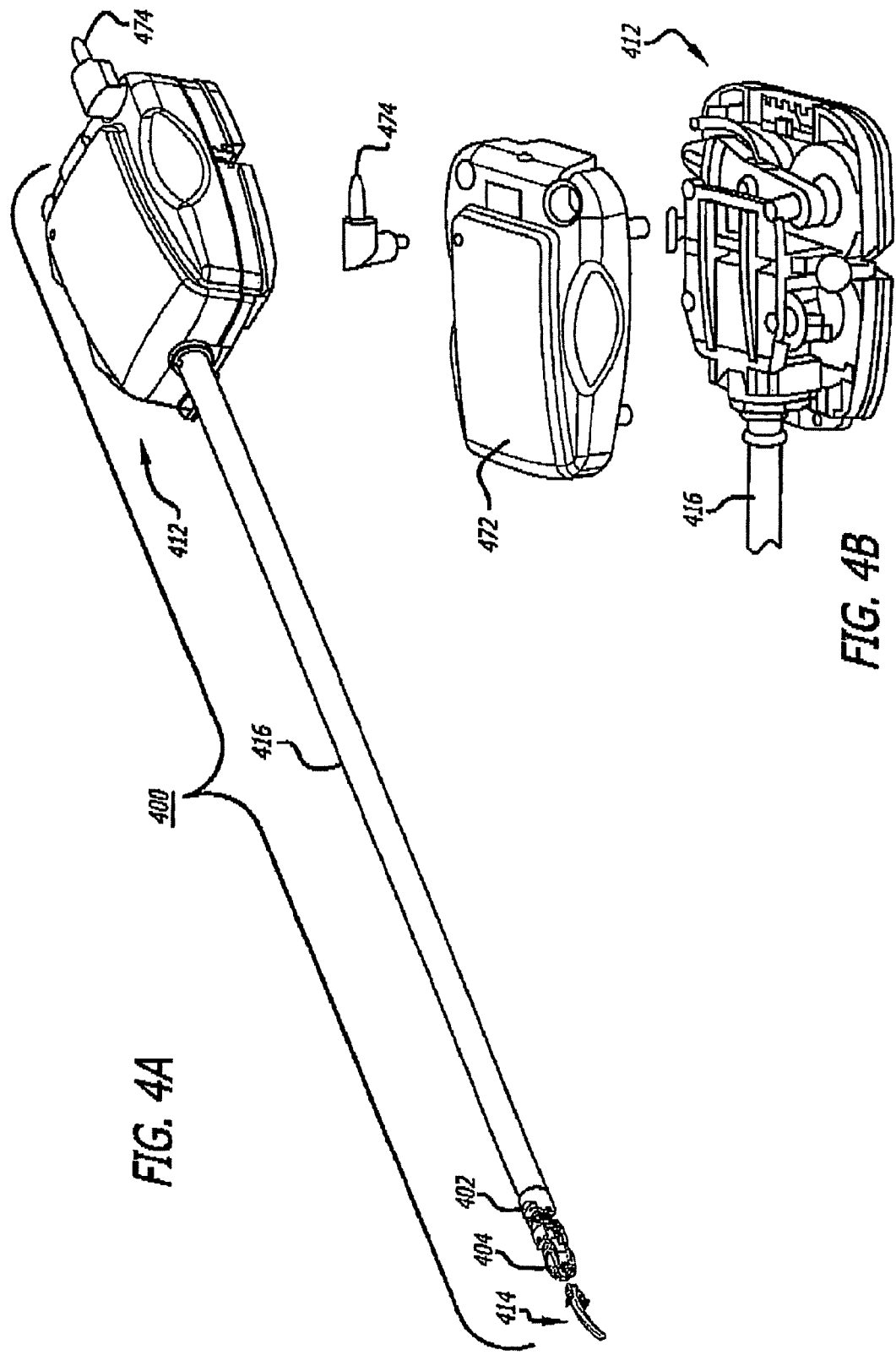

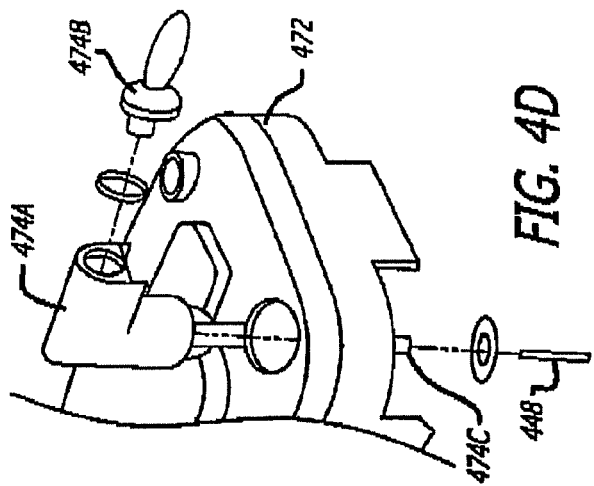
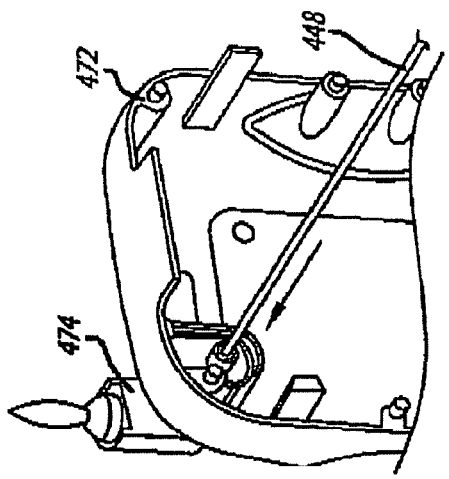
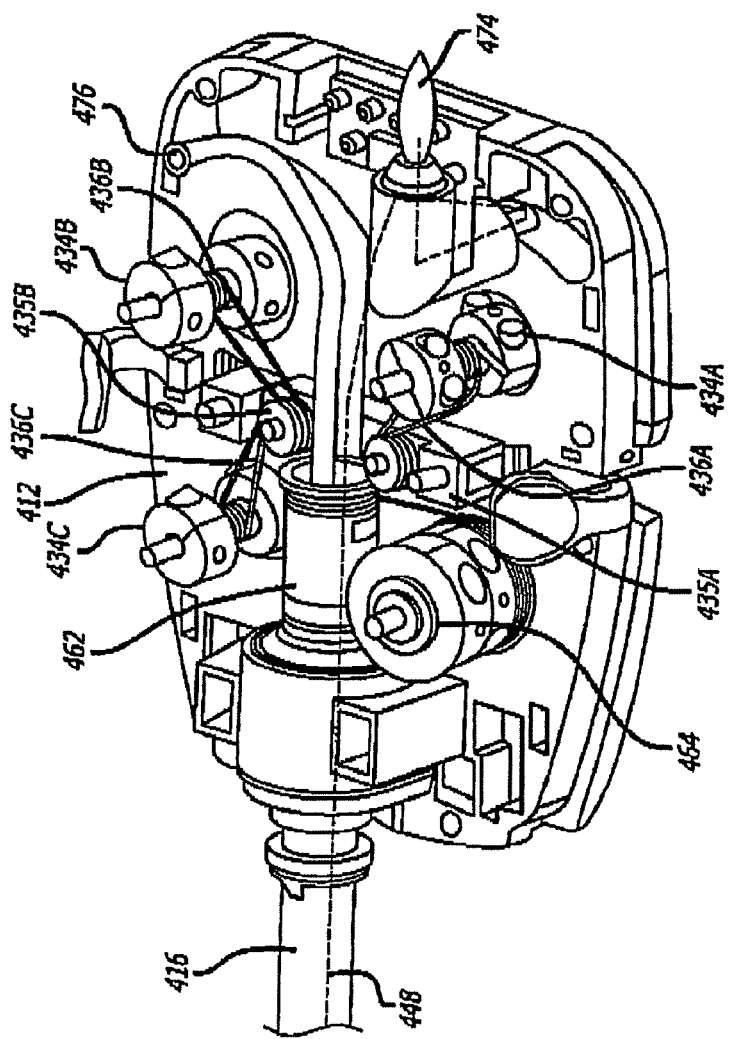
FIG. 4D
FIG. 4E
FIG. 4C

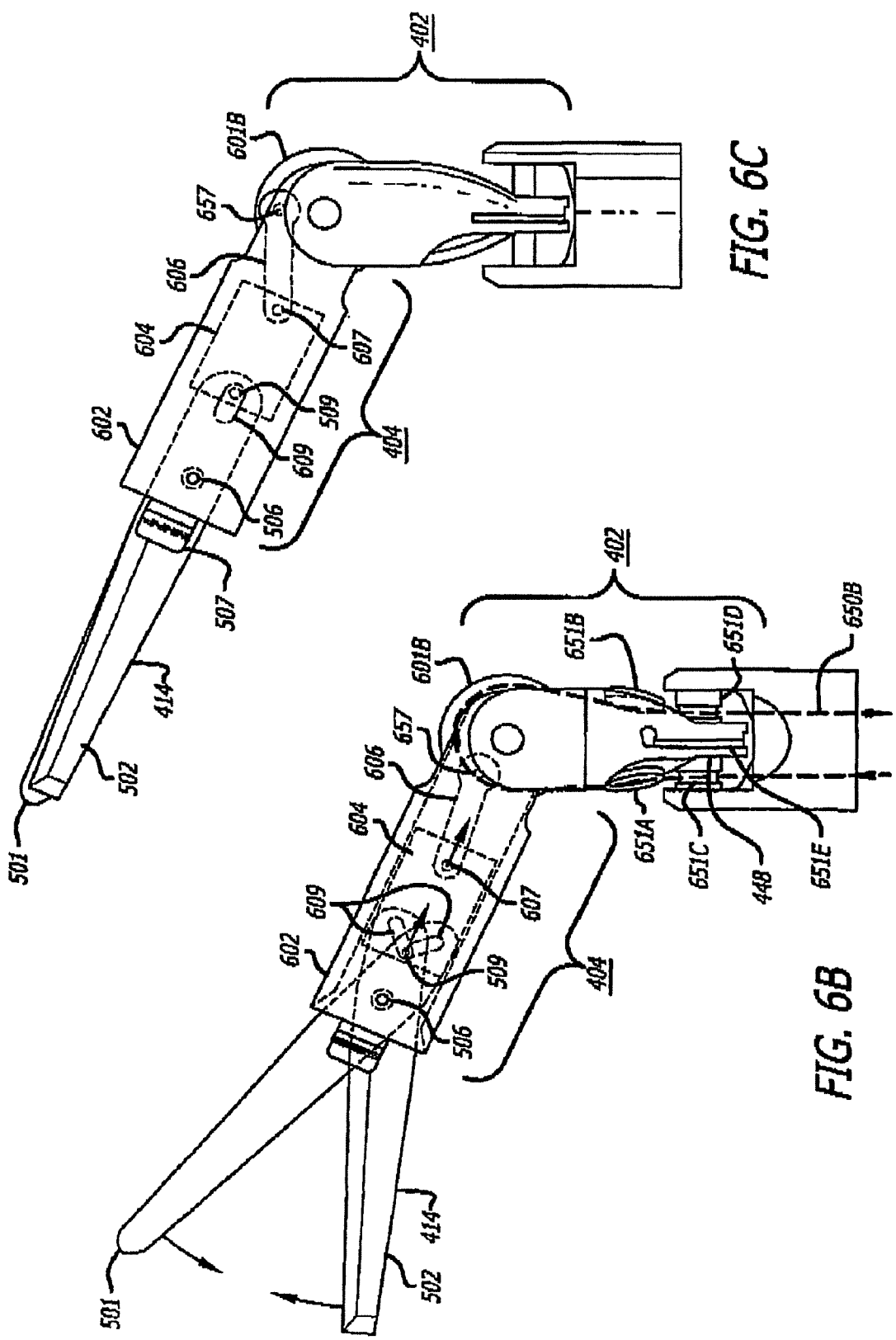

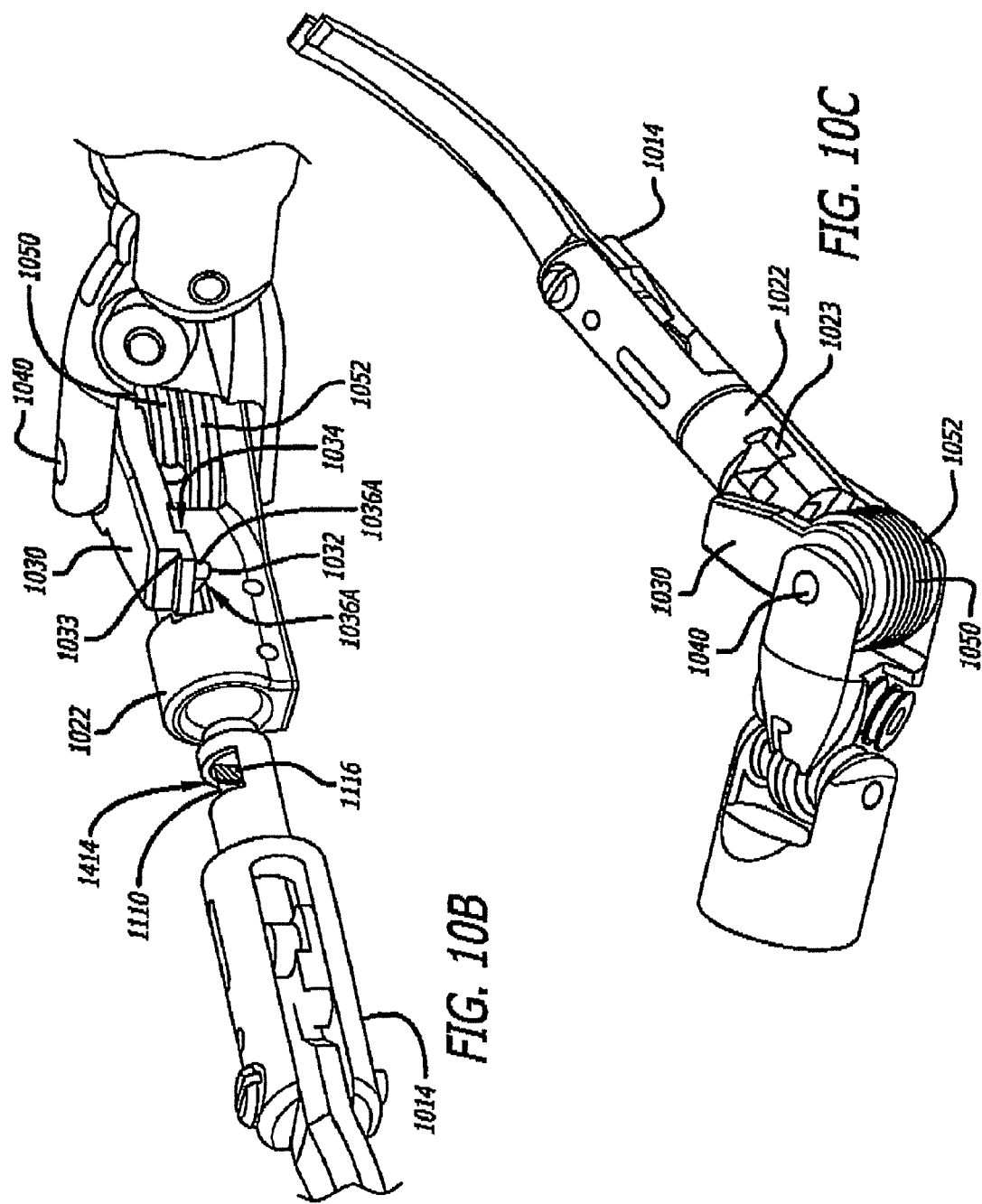

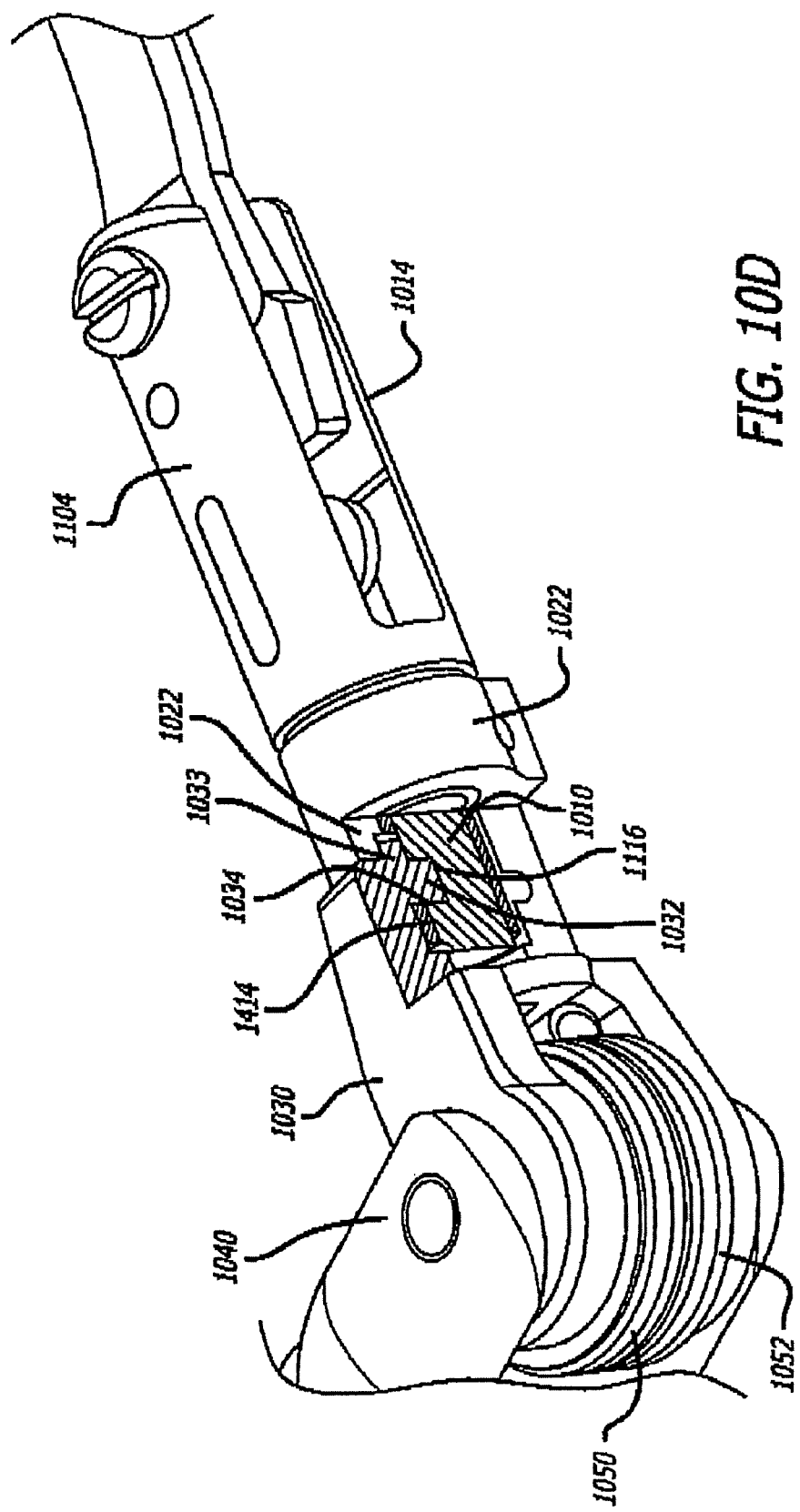

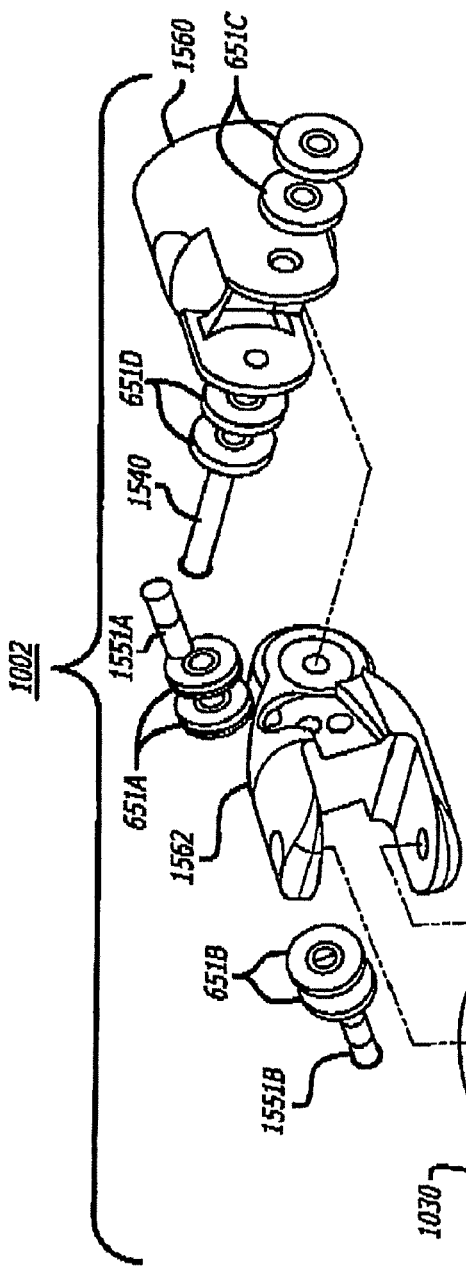
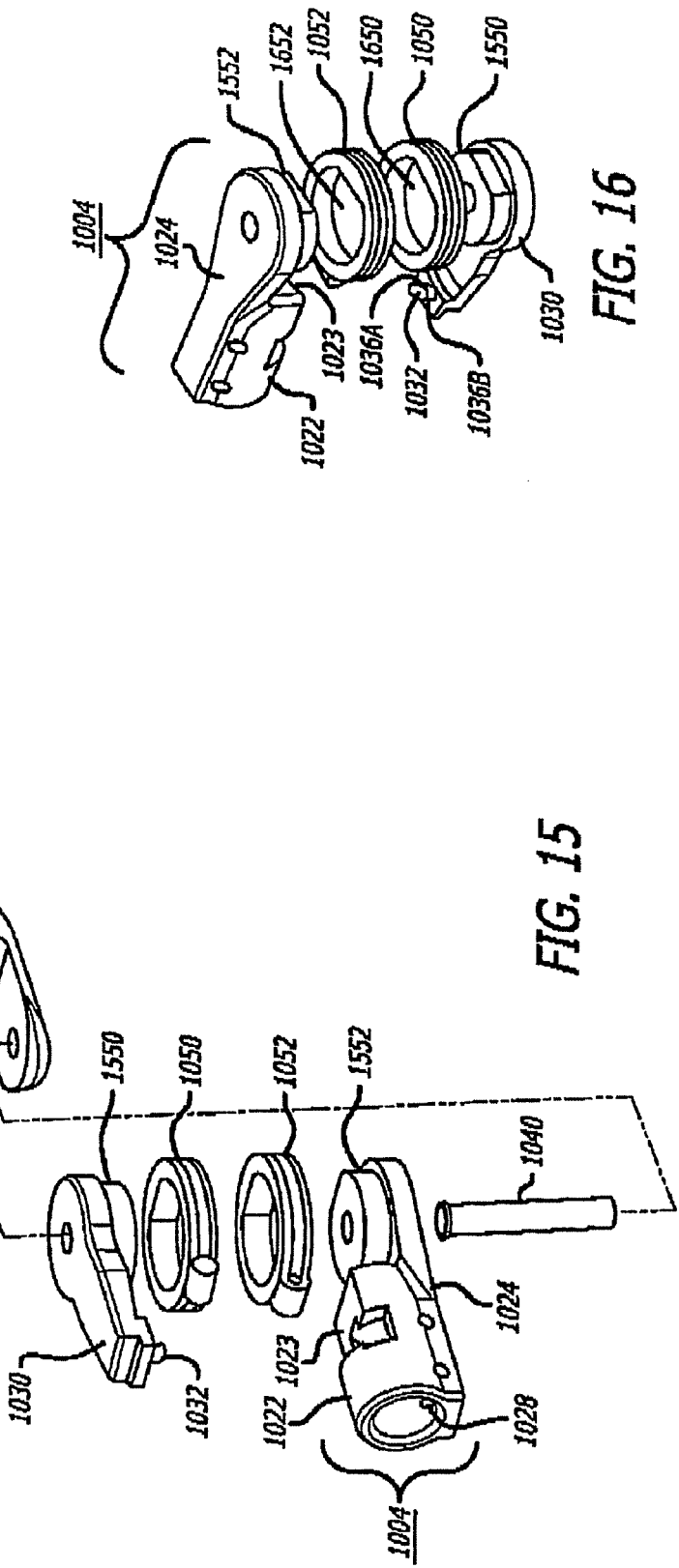
FIG. 15
FIG. 16

METHODS FOR REPLACEABLE END-EFFECTOR CARTRIDGES

CROSS-REFERENCE TO RELATED APPLICATIONS

This non-provisional United States (U.S.) patent application claims the benefit of and is a divisional of U.S. patent application Ser. No. 11/238,794 filed on Sep. 28, 2005 by inventor Scott Manzo, entitled WRISTED ROBOTIC TOOL WITH REPLACEABLE END-EFFECTOR CARTRIDGES, pending, which is a continuation in part of U.S. patent application Ser. No. 10/126,451 filed on Apr. 18, 2002 by inventor Scott Manzo, entitled "ROBOTIC TOOL WITH MONOPOLAR ELECTRO-SURGICAL SCISSORS", now issued as U.S. Pat. No. 6,994,708, the full disclosure of which is incorporated herein by reference, and further claims the benefit of and is a continuation in part of U.S. patent application Ser. No. 10/611,411 filed on Jun. 30, 2003 by inventors Scott Manzo, et al., entitled "ELECTRO-SURGICAL INSTRUMENT WITH REPLACEABLE END EFFECTORS AND INHIBITED SURFACE CONDUCTION", now issued as U.S. Pat. No. 7,367,973, the full disclosure of which is also incorporated herein by reference; and this application further claims the benefit of U.S. Provisional Patent Application No. 60/617,341 entitled "ROBOTIC TOOL WITH WRISTED MONOPOLAR ELECTROSURGICAL SCISSORS" filed on Oct. 8, 2004 by inventor Scott Manzo, et al., the full disclosure of which is incorporated herein by reference.

Additionally, this non-provisional U.S. patent application is related to U.S. patent application Ser. No. 11/238,698 filed on Sep. 28, 2005 by inventors Scott Manzo, et al., entitled "WRISTED ROBOTIC SURGICAL TOOL FOR PLUGGABLE END EFFECTORS", pending; and U.S. patent application Ser. No. 11/094,639 filed on Mar. 30, 2005 by inventors Scott Manzo, et al., entitled "ROBOTIC TOOL WITH WRISTED MONOPOLAR ELECTROSURGICAL END EFFECTORS", pending.

FIELD

The embodiments of the invention are generally related to surgical instruments or tools. More particularly, the embodiments of the invention relate to robotic surgical instruments and systems that include electrosurgical end effectors and methods of performing a robotic surgical procedure.

BACKGROUND

After surgery on a patient, durable surgical instruments may generally be replaced, if inexpensive, or sterilized and repaired for reuse in another surgical procedure, if expensive. For example, a cutting blade of a metal scalpel or surgical knife may become dull after completion of a surgery. Instead of repairing and sterilizing the dull scalpel, a hospital may replace it with a new metal scalpel. Generally manual surgical instruments are less expensive and may be subject to replacement than more automated surgical equipment used in surgery, such as a laparoscope for example.

To make the more expensive automated surgical equipment more attractive for use in more hospitals, it is desirable to reduce the maintenance and replacement costs of the more automated surgical equipment after surgery.

BRIEF SUMMARY

The embodiments of the invention are best summarized by the claims that follow below. However briefly in accordance with aspects of one embodiment of the invention, a method is disclosed including coupling a replaceable end effector cartridge to a receptacle of a robotic surgical tool; translating a rotational motion into a linear motion; and pivoting an end effector of the replaceable end effector cartridge in response to the linear motion.

BRIEF DESCRIPTIONS OF THE DRAWINGS

FIGS. 4A-4E illustrate an exemplary electro-surgical instrument or tool with a replaceable end effector cartridge.

FIGS. 6B-6C illustrate top views of the replaceable end effector cartridge of FIG. 6A mounted to the robotic surgical tool and actuated to an open and closed position respectively.

FIGS. 10A-10D illustrate views of a second embodiment of a replaceable end effector cartridge mounted and dismounted with a robotic surgical tool.

FIG. 15 illustrates a magnified exploded view from the side of the elements of the mechanical wrist of the robotic surgical tool of FIGS. 10A-10D.

FIG. 16 illustrates a magnified exploded view from the bottom of some of the elements of the mechanical wrist of the robotic surgical tool of FIGS. 10A-10D.

DETAILED DESCRIPTION

In the following detailed description of the embodiments of the invention, numerous specific details are set forth in order to provide a thorough understanding of the invention. However, it will be obvious to one skilled in the art that the embodiments of the invention may be practiced without these specific details. In other instances well known methods, procedures, components, and circuits have not been described in detail so as not to unnecessarily obscure aspects of the embodiments of the invention.

The embodiments of the invention provide methods, apparatus and systems for replaceable electrosurgical end effectors in robotically controlled minimally invasive surgical operations. In particular, electrosurgical cutting/shearing instruments and systems, as well as methods of performing minimally invasive robotic surgical procedures with such instruments are provided. The instruments of the embodiments of the invention are capable of treating tissue with heat produced by electrical energy while cutting, shearing, grasping, engaging, or contacting treatment tissue. The electrosurgical treatment may further reduce bleeding of tissue by cauterizing tissue and coagulating blood, or achieve various other desired effects on the treatment tissue. The electrosurgical treatment is carried out in a safe and effective manner that incorporates a variety of safety features to prevent current leakage to non-target tissue so as to reduce collateral tissue damage, unwanted burning, or the like.

Figure 1:
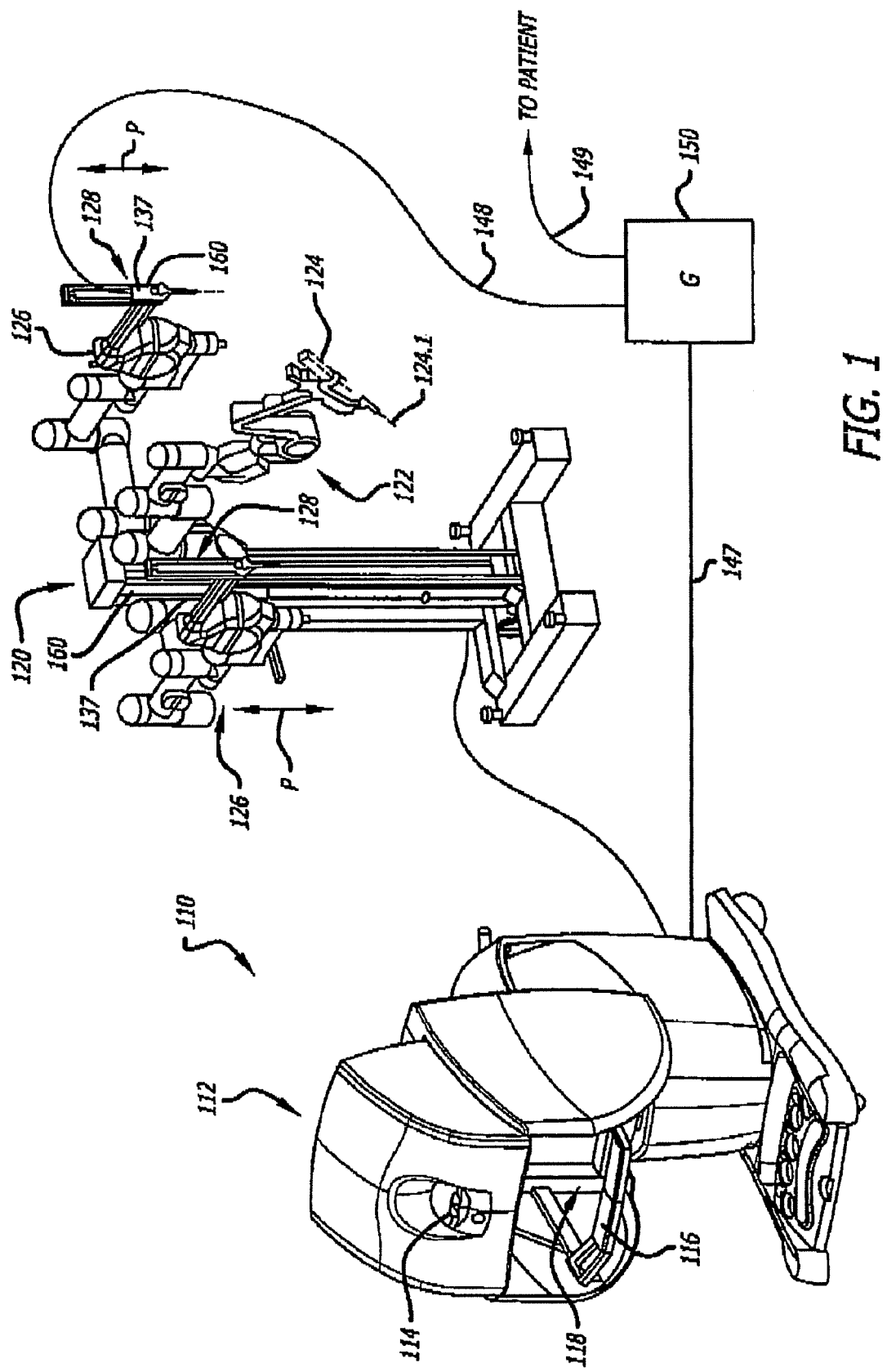
FIG. 1 is a perspective illustration of a robotic surgical system with which various embodiments of the invention may be used.

Referring now to FIG. 1, a robotic surgical system 110 generally includes a user-operated control station or "surgeons console" 112 and a surgical work station or "cart" 120. The control station 112 includes an image display module 114 for displaying an image of a surgical site, a support 116 on which an operator may rest his/her forearms, and a space 118 where two master control devices are located (not shown). When using control station 112, a surgeon or other user typically sits in a chair in front of control station 112, views the surgical site through the display module 114, and grips the master controls one in each hand while resting the forearms on support 116. An exemplary robotic surgical system as described in FIG. 1 is the DA VINCI™ system available from Intuitive Surgical, Inc. of Mountain View, Calif.

Control station 112 is generally coupled to cart 120 such that commands from the master controls may be transmitted to the cart 120. In use, cart 120 is positioned adjacent a patient requiring surgery and is then normally caused to remain stationary until a surgical procedure to be performed by means of surgical system 110 has been completed. Cart 120 typically has wheels or castors to render it mobile. Control station 112 is typically positioned remote from cart 120 and in some embodiments may be separated from cart 120 by a great distance, for example miles away, but will typically be used within an operating room with the cart 120.

In various embodiments, cart 120 includes at least three robotic arm assemblies 122, 126, 126, one of which is configured to hold an image capture device 124 and the others of which are configured to hold surgical instruments 128. Alternatively, the cart may include more or fewer than three robotic arm assemblies and the robotic arm assemblies may be configured to hold any suitable tool, instrument, imaging device and/or the like. Image capture device 124 may include any suitable device, such as an endoscope, fiber optic camera, or the like. Image capture device 124 generally includes an object viewing end 124.1 at a remote end of an elongate shaft configured to enable the viewing end 124.1 to be inserted through an entry port in a patient's body to capture an image of the surgical site.

Coupling of cart 120 to control station 112 generally enables display module 114 to display an image captured by image capture device 124. Coupling of cart 120 to control station 112 also typically allows each of the master controls on the control station 112 (not shown) to control one robotic arm assembly 126 and one surgical instrument 128. In various embodiments, each master control may alternatively be used to control more than one robotic arm assembly 126 and/or more than one surgical instrument 128.

Surgical instruments 128 on the robotic arm assemblies 126 typically include elongate shafts, with proximal and distal ends. End effectors are generally mounted on wrist-like mechanisms pivotally mounted on the distal ends of the shafts, for enabling the instruments 128 to perform one or more surgical tasks. Generally, the elongate shafts of surgical instruments 128 allow the end effectors to be inserted through entry ports in a patient's body so as to access the internal surgical site. Movement of the end effectors is generally controlled via master controls on the control center 112.

Figure 2:
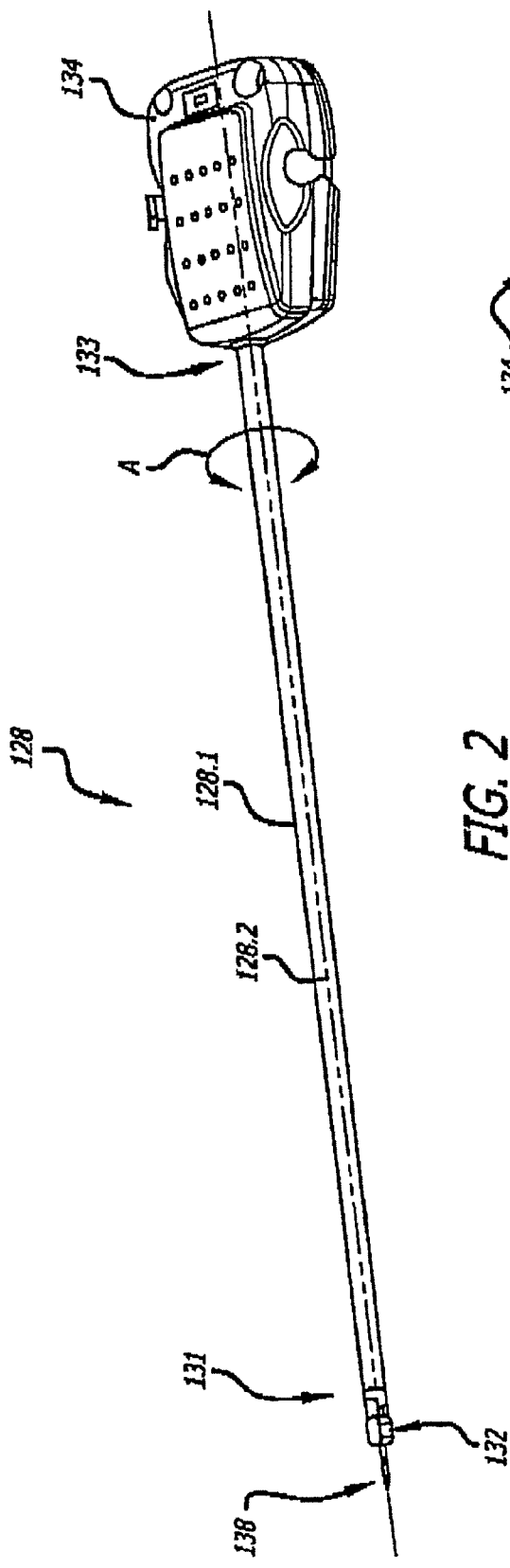
FIG. 2 is a perspective illustration of a robotic surgical tool that may be used with the robotic surgical system of FIG. 1.

Referring now to FIG. 2, surgical instrument 128 generally includes an elongate shaft 128.1 having a proximal end 133 and a distal end 131, a pivot 132, an end effector 138 disposed at the distal end, and an instrument base 134 disposed at the proximal end. Base 134 is generally configured to releasably engage an interface member of the robotic surgical system, such as robotic surgical system 110 in FIG. 1. In general, instrument 128 is engaged with the system via base 134 (base not shown in FIG. 1) such that instrument 128 is releasably mountable on a carriage 137 which can be driven to translate along a linear guide formation 160 of the arm 126 in the direction of arrows P.

Figure 3:
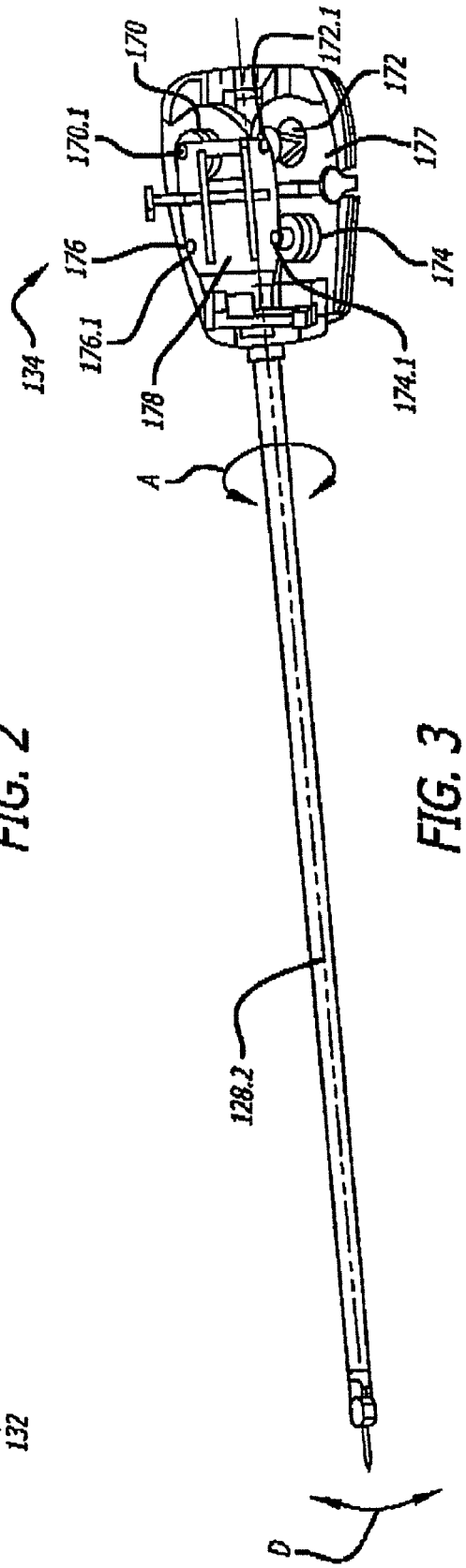
FIG. 3 is a perspective illustration of the robotic surgical tool in FIG. 2, with a cover of a tool base removed to show internal structures of the tool base.

With reference to FIGS. 2 and 3, shaft 128.1 is rotatably mounted on base 134 for rotation about an axis 128.2 extending longitudinally along the shaft 128.1 as indicated by the arrows A. Thus, when mounted on an arm assembly 126, end effector 138 may have a plurality of degrees of freedom of movement relative to manipulator arm 126, in addition to actuation movement of the end effector itself. The instrument may be translated along an insertion axis (Arrows P in FIG. 1). Typically, the instrument degrees of freedom include rotation about the axis 128.2 as indicated by arrows A, and in the case of instruments 128 including pivots 132, angular displacement as a whole about pivot 132 as indicated by arrows D. Alternatively, the distal pivoting degree of freedom may be omitted. A single pivot wrist, a multi-pivot wrist, a distal roll joint mechanism, or other joints or wrist-like mechanisms may be included to provide additional operational degrees of freedom to the end effector. Movement of end effector 138 relative to manipulator arm 126 controlled by appropriately positioned actuators, such as electric motors, or the like, which respond to inputs from an associated master control at the control station 112, so as to drive the end effector 138 to a required orientation as dictated by movement of the associated master control.

Referring now to FIG. 3, base 134 of surgical instrument 128 suitably includes transmission members 170, 172, 174, and 176, which include spools secured on shafts 170.1, 172.1, 174.1, and 176.1. Ends of shafts 170.1, 172.1, 174.1, 176.1 generally extend from a side 177 of base 134 to a mounting plate 178 within base 134 and are configured to rotate. Generally, the ends of shafts 170.1, 172.1, 174.1, 176.1 at side 177 of base 134 extend through side 177, to an outer surface of side 177 (not shown). At the outer surface, each shaft 170.1, 172.1, 174.1, 176.1 includes an engaging member (not shown) configured to releasably couple with a complementary engaging member (not shown) rotatably mounted on the carriage 137 of a robotic arm assembly 126 (see FIG. 1). The engaging members on carriage 137 are generally coupled to actuators (not shown), such as electric motors or the like, to cause selective angular displacement of each engaging member on the carriage 137 in response to actuation of its associated actuator. Thus, selective actuation of the actuators is transmitted through the engaging members on the carriage 137, to the engaging members on the opposed ends of the shafts 170.1, 172.1, 174.1, 176.1 to cause selective angular displacement of the spools 170, 172, 174, 176. Where more or fewer degrees of freedom are desired, the number of spools may be decreased or increased.

Electrosurgical Tool with Replaceable End Effector Cartridge

FIGS. 4A through 8B illustrate one embodiment of a robotic electrosurgical tool 400 including a disposable or replaceable end effector cartridge. These figures are for illustration purposes and do not necessarily reflect the actual shape, size, or dimensions of the robotic electrosurgical instrument or tool nor the disposable or replaceable end effector cartridge.

Referring now to FIGS. 4A-4C, the robotic electro surgical tool 400 including a disposable or replaceable end effector cartridge 414 for use with the minimally invasive robotic surgical system of FIG. 1 is illustrated. The end effector cartridge 414 is replaceable so that it can be readily cleaned and/or replaced when dull by fresh sharp end effectors.

The robotic electrosurgical tool 400 includes an elongated shaft 416 having a proximal end and a distal end, a disposable or replaceable end effector cartridge 414, and an interface or tool base 412 coupled to the proximal end of the shaft 416 and removably connectable to the robotic surgical system.

At the distal end of the shaft 416 is a mechanical wrist 402 and a receptacle 404. The orientation of the mechanical wrist 402 is controlled through pulleys in the tool base 412 and the wrist 402 with cables of cable loops wrapped around each being routed through the shaft 416. The robotic system causes the pulleys in the tool base 412 to be rotated in order to control the position of the mechanical wrist 402, the receptacle 404, and a cartridge 414 coupled into the receptacle. Thus, the cable of the cable loops may also be referred to as a control cable.

Further details of mechanical wrists that may be applicable to the mechanical wrist 402 are described in U.S. Pat. Nos. with filing dates and named inventor as follows U.S. Pat No. 5,792,135, May 16, 1997, Madhani et al; U.S. Pat No. 5,979,900, May 16, 1997, Madhani et al; U.S. Pat No. 5,807,377, May 16, 1997, Madhani et al; U.S. Pat No. 6,206,903, Oct. 8, 1999, Ramans; U.S. Pat No. 6,312,435, Oct. 8, 1999, Wallace et al.; U.S. Pat No. 6,371,952, Jun. 28, 1999, Madhani et al; U.S. Pat No. 6,394,998, Sep. 17, 1999, Wallace et al.; U.S. Pat No. 6,676,684, Sep. 4, 2001, Morley et al.; U.S. Pat No. 6,685,698, Jan. 10, 2003, Morley et al.; U.S. Pat No. 6,699,235, Mar. 2, 2004, Wallace et al.; U.S. Pat No. 6,746,443, Jul. 27, 2000, Morley et al.; U.S. Pat No. 6,817,974, Jun. 28, 2002, Cooper et al.; and application Ser. No. 10/726,795, Pub. No.: US 2004/0138700 A1, Dec. 2, 2003, Cooper et al., all of which are incorporated herein by reference.

The receptacle 404 receives the disposable or replaceable end effector cartridge 414 and includes an actuator to actuate the end effectors. In the parent patent application, U.S. patent application Ser. No. 10/126,451, the end effectors were actuated by the mechanical movement of a rod within the shaft from the interface or tool base. In contrast, the end effectors in the cartridge 414 in this case may be actuated from the tool base 412 through a cable loop, pulleys, and a spool similar to how other elements of the wrist 402 are controlled.

The disposable or replaceable end effector cartridge 414 is used in performing a surgical operation such as cutting, shearing, grasping, engaging, or contacting tissue adjacent a surgical site. Preferably, in one embodiment of the invention, the replaceable end effector cartridge 414 includes a pair of scissor-like blades (see blades 501-502 illustrated in FIG. 5A, for example) for cooperatively shearing the tissue. Additionally, a conductor electrically communicating with at least one blade delivers electrical energy to tissue engaged by the blades.

As shown in FIG. 4B, the tool base 412 may be enclosed by a cover 472 which mounts an electrical connector 474 for the conductor to permit connection to an electrosurgical generator G 150 illustrated in FIG. 1.

Referring momentarily back to FIG. 1, the electrosurgical generator G 150 is a part of the robotic surgical system 110. The electrosurgical generator G 150 is controlled through the control station 112 over the control cable 147 by a surgeon operating the control station. One or more wires are routed within a cable 148 that is coupled to the electrical connector 474. In the case of a monopolar system, one wire is routed within the cable 148 to the electrical connector 474 and a ground wire 149 is coupled to the patient. In the case of a bipolar system, two wires are routed within the cable 148 to the electrical connector 474 and the ground wire 149 is not used.

Referring now to FIG. 4C, an insulated conductor 448, a wire, passes out from the shaft 416 to the rear of the base 412 to the electrical connector 474 for connection to the electrosurgical generator G 150.

As discussed previously, the end effectors in the cartridge 414 are actuated from the tool base 412 through a cable of a cable loop, pulleys, and a spool. The tool base 412 includes spools 434A-434C, guide pulleys 435A-435B, and cable loops 436A-436C to control the mechanical wrist 402 and the end effectors of the replaceable end effector cartridge 414.

A cable loop is a single cable routed in a loop around the drive pulley from the spool in the tool base. A cable loop may be formed by joining or splicing different segments of cable together. The cables of the cable loops 436A-434C are routed from the spools over the guide pulleys 435A-435B and through the shaft 416 to drive pulleys in the wrist 402. The tool base 412 further includes a spool 464 and a drum 462 with a cable loop coupled there-between to control the rotation of the shaft 416 and the wrist 402.

A first end of the cable of each cable loop is wrapped in one direction around the spool with the second end of the cable wrapped in an opposite direction around the same spool. In this manner, one end of cable is taken up while the other end of the cable is released during the rotation of a spool. Each spool includes a tension mechanism to avoid slack in the cable of each cable loop.

The shaft of each spool extends through the tool base 412 to its underside to couple to an engaging member. The engaging member can releasably couple to a complimentary engaging member that is in turn coupled to an actuator of the surgical system, such as an electric motor, to cause an angular displacement in the spool in response to a control signal from the control console.

An optional flush tube 476 may be mounted to a tool base cover 472 by a flush port 478 and the assembled base 412. The flush tube preferably extends forward (distally) within the base 412 to communicate with the shaft 416 to permit fluids to be passed through the shaft 416 and/or to pressurize the shaft 416. For example, introduction of insufflation gas during surgery or the introduction of cleaning or sterilization gases or fluids prior and/or subsequent to surgery may be passed to the shaft 416 via flush tube 476. U.S. Pat. No. 6,004,509 describes the use of fluids and gases to maintain sterility of a surgical instrument, and is incorporated herein by reference.

Referring now to FIGS. 4D and 4E, the base cover 472 mounts an electrical connector 474, in this case banana clip assembly 474a, 474b, and 474c, for the insulated conductor 448 to permit connection to the electrosurgical generator G 150. Note that the connections described above provide an insulated continuous electrical path from the base connector 474 to the scissors blades 501 and 502, protected from tissue contact except at the blades 501, 502. Energization of the blades is controllable by the surgeon.

Replaceable End Effector Cartridge for Piston Actuator

Referring now to FIGS. 5A and 6A-6C, the disposable or replaceable end effector cartridge 414 can be mounted into the receptacle 404 at the distal end of the shaft 416, as previously discussed. The disposable or replaceable end effector cartridge 414 can also be dismounted from the receptacle 404 so that it can be replaced with a new cartridge.

In one embodiment of the invention, the disposable or replaceable end effector cartridge 414 includes one fixed and one movable end effectors or two movable end effectors 501-502; a drive sleeve 504; a pivot bolt (with or without a nut), screw, or rivet 506; a spring latch 507; an L-shaped slot 508; and a cam-slot pin or actuating pin 509 coupled together as shown.

The end effectors 501-502 include a base region, an off-center region, and an end region. Near the off-center region, the screw or rivet 506 rotatably couples the end effectors 501-502 together at a pivot point. The screw or rivet 506 may also rotatably couple the spring latch 507 together with the end effectors 501-502 at the pivot point. That is, at the pivot point the screw or rivet 506 is mounted to the spring latch 507. The spring latch 507 includes a catch 517 to engage a recess in the receptacle 404. The spring latch 507 can be flexed to remove the catch 517 from the recess in the receptacle to replace the cartridge.

The base region of one or each of the end effectors 501-502 may include a cam slot (see cam slots 609 illustrated in FIG. 6B) slidingly engaged with the cam-slot pin or actuating pin 509 to rotate the end effectors about the bolt, screw or rivet 506. With both end effectors having a cam slot 609 in the base region, they are crossed over each other to form a pair of crossed cam slots 609. The base regions of the end effectors couple to a fork element or drive sleeve 504 that bears the cam slot pin 509. The fork element or drive sleeve 504 engages the piston 604 via the "L" shaped slot 508 and pin 608.

Internally, the drive sleeve 504 is slotted to slidingly receive the base region of the end effectors 501-502. Externally, the drive sleeve 504 includes the L-shaped slot 508 near its base region to interface to the drive pin 608 that is rigidly coupled to a piston 604. Moreover, the cam-slot pin or actuating pin 509 is slidingly fitted into the cam slots 609 and coupled at each of its ends to sides of the drive sleeve 504. In this manner, the drive sleeve 504 may be slidingly coupled to one or both of the end effectors 501-502.

In a preferred embodiment, the one or both of the movable end effectors 501-502 includes a pair of blades of a shear or scissors at their end regions, as is discussed previously. In which case, the pivot bolt or screw 506 may be adjustable, such as an adjustable screw, to obtain a desired shearing action.

Figure 5A:
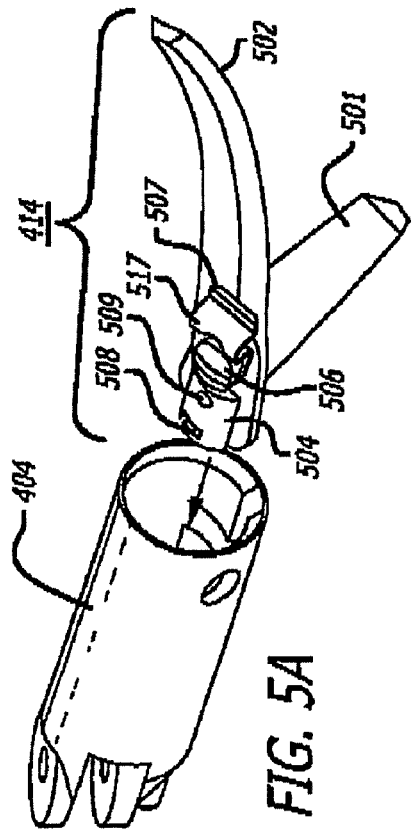
FIGS. 5A-5C illustrate perspective views as to how a replaceable end effector cartridge may be mounted and dismounted from a robotic surgical tool in one embodiment of the invention.
Figure 5B:
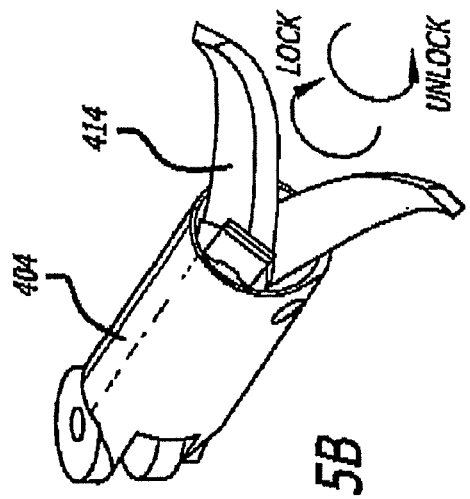
Figure 5C:
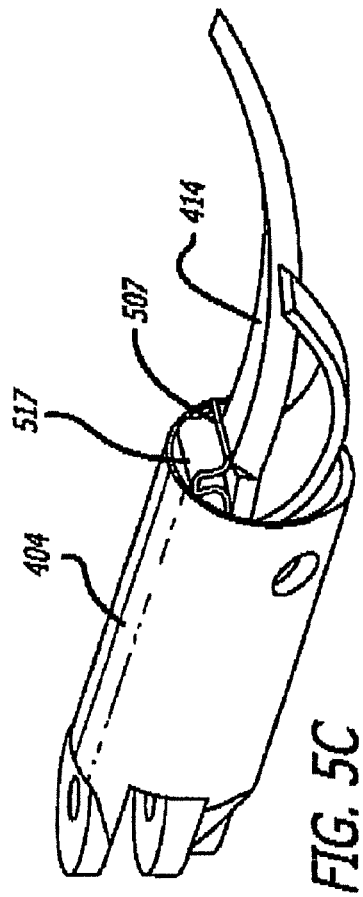

Referring now to FIGS. 5A-5C, to mount the disposable or replaceable end effector cartridge 414, a drive end of the cartridge is plugged into an open end of the receptacle 404 with the screw 506 aligned with an initial portion of an L-shaped slot 616 of an inner sleeve 610 and the drive pin 608 in proper alignment with an initial portion of the L-shaped slot 508 in the drive sleeve 504. As illustrated by FIG. 5B, the cartridge 414 is then rotated in one direction (clockwise for example as illustrated by the lock arrow) so that the screw 506 engages the second portion of the L-shaped slot 616 and the drive pin 608 of the piston engages the second portion of the L-shaped slot 508 in the exterior surface of the drive sleeve 504. During rotation, the spring latch 507 snaps into a recess (see recess 617 in FIGS. 6A and 7A) of the inner sleeve 610 within the receptacle and locks the cartridge 414 in place deterring further rotation, as is illustrated by FIG. 5B. The degrees of rotation of the cartridge 414 to lock it in place may be forty-five degrees, more or less, for example. In FIG. 5C, the cartridge 414 is finally mounted and locked in place within the receptacle 404.

To dismount the disposable or replaceable end effector cartridge 414, the spring latch 507 is depressed to release it from the recess 617 of the inner sleeve 610. The spring latch 507 can be readily depressed with a needle driver or a clamp. The cartridge is then rotated in the opposite direction (counter-clockwise for example as illustrated by the un-lock arrow in FIG. 5B) so that the latch 507 is no longer in alignment with the recess 617 of the inner sleeve 610. The drive end of the cartridge is then un-plugged or removed from the open end of the receptacle 404.

As discussed previously, the disposable or replaceable end effector cartridge 414 is used in performing a surgical operation such as cutting, shearing, grasping, engaging, or contacting tissue adjacent a surgical site. The end effectors 501-502 may be blades of a shear or scissors in one embodiment of the invention. In another embodiment of the invention, the end effectors 501-502 may be the jaws of a gripper to grasp, engage or contact tissue. The end effectors 501-502 may take on other known surgical functions. As the replaceable cartridge defines the function of the robotic surgical tool, the type and function or cartridge may be interchangeable.

Wristed Receptacle with Piston Actuator

Figure 6A:
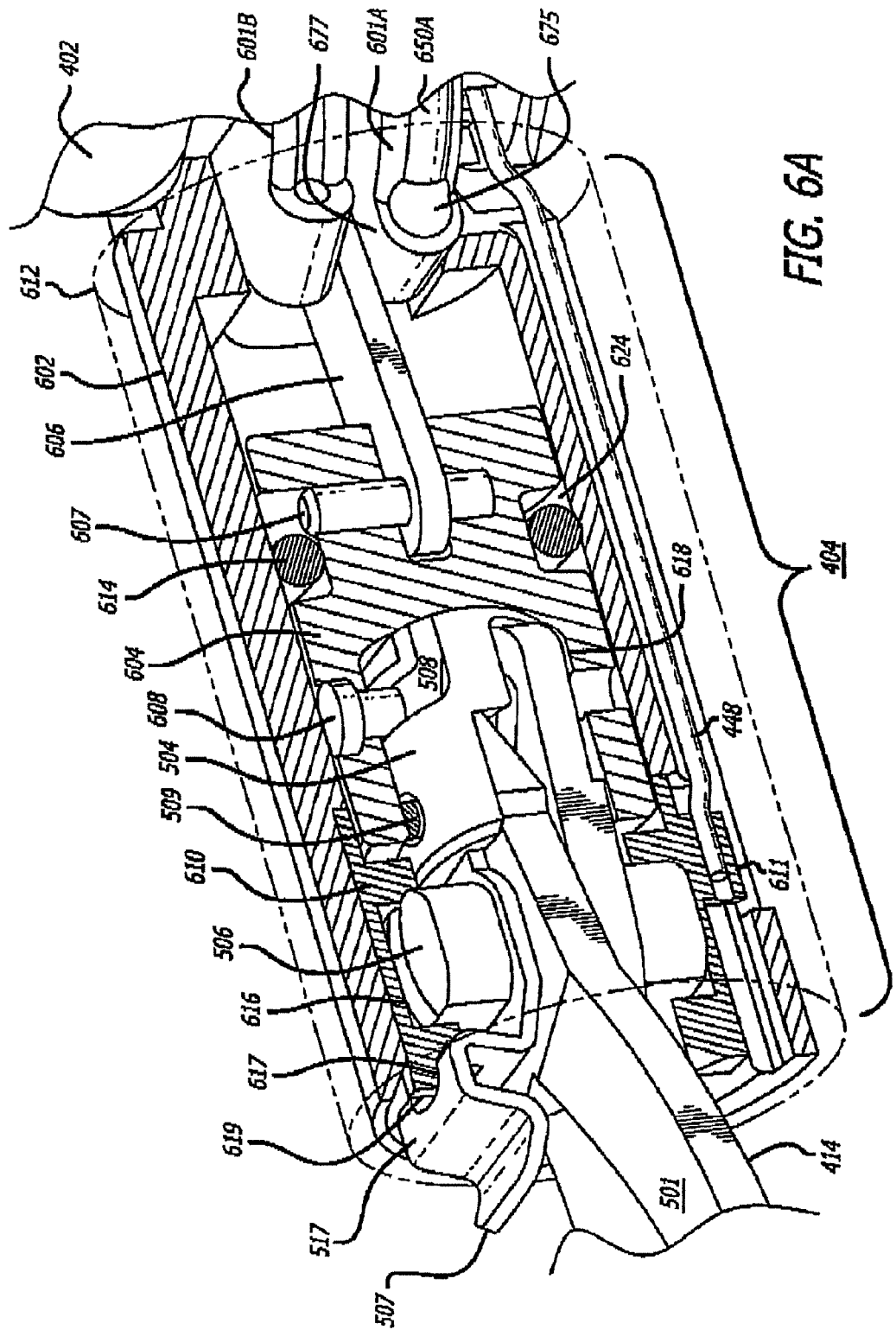
FIG. 6A illustrates a magnified cutaway view of a replaceable end effector cartridge mounted to the robotic surgical tool in one embodiment of the invention.
Figure 8A:
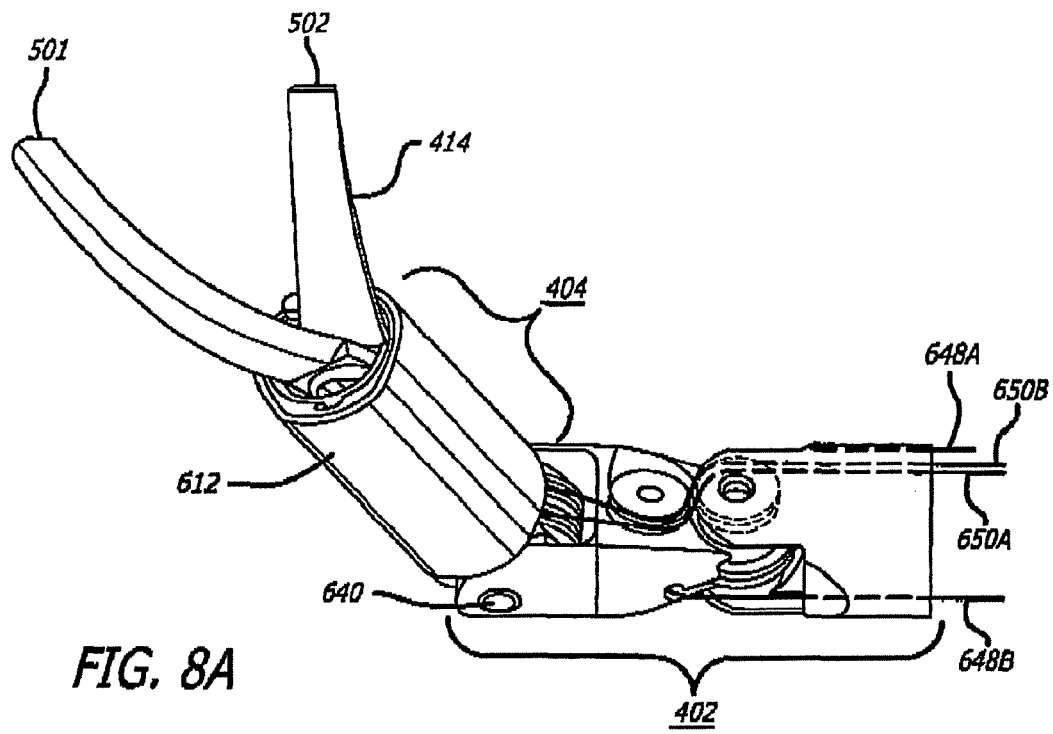
FIGS. 8A-8B illustrate movement of the wrist and replaceable end effector cartridge from one position to another.
Figure 8B:
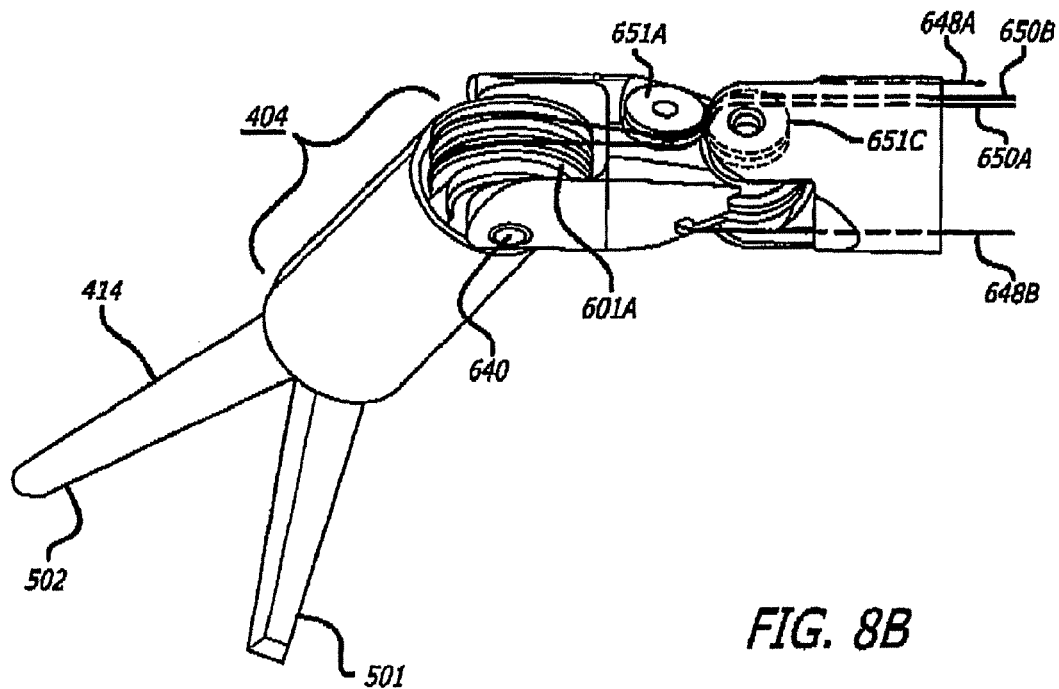

Referring now to FIGS. 6A-6C, the receptacle 404 is coupled to the wrist 402 and rotated by a drive pulley 601A coupled to a cable of a cable loop 650A routed within the shaft from the tool base. A crimped sleeve 675 around the cable of the cable loop 650A fastens the cable to a boss 677 of the drive pulley 601A to couple the cable loop and the pulley together. Other cable loops may be similarly coupled to a drive pulley. The pulley 601A yaws (e.g., left and right, or up and down) the cylinder and scissors as a unit at the wrist 402 as illustrated in FIGS. 8A-8B. Therefore, the receptacle 404 may also be referred to as a wristed receptacle.

The wristed receptacle 404 includes a cylinder 602, a piston 604, and a connecting rod 606. The piston 604 is slidingly engaged within the cylinder 602. One end of the connecting rod 606 is rotatably coupled to the piston 604 by a piston pin 607. The opposite end of the connecting rod 606 is coupled to a drive pulley 601B by means of a crank pin 657 (see FIGS. 7A-7B). A cable of a cable loop 650B is routed from the tool base through the shaft and coupled to the drive pulley 601B for the system to control the end effectors, as illustrated in FIGS. 6B-6C for example. The connecting rod 606 and piston 604 assembly engages a cam mechanism of the cartridge 414 to actuate the end effectors 501-502 or blades of scissors in a preferred embodiment of the invention.

With the cartridge 414 mounted to the receptacle 404, the pivot point of the end effectors 501-502 at the screw 506 is fixed in relation to the cylinder 602, while the base regions of the end effectors forming the fork are free to slide reciprocally with the piston 604, thus actuating the cam mechanism of the cartridge.

Pulley 601B reciprocates the connecting rod 606 which in turn moves the piston 604 in the cylinder 602. The piston 604 is coupled to the drive sleeve 504 and drive pin 508 when the cartridge 414 is mounted in the receptacle 404. Thus, movement in the piston 604 also moves the drive sleeve 504 and the drive pin 509 in one or both of the pair of crossed cam slots 609 in the base region of each end effector. (see also FIGS. 9A-9B and the description thereof) The cam slots 609 are on an angle with a centerline of each end effector such that linear motion of the drive pin 509 causes a rotational motion in the end effector 501-502. With the piston 604 in a fully forward position, the end effectors 501-502 may be driven by the drive pin 509 to a fully open position as illustrated in FIG. 6B. With the piston 604 cranked back to a fully backward position, the end effectors 501-502 may be driven by the drive pin 509 to a fully closed position as illustrated in FIG. 6C.

Figure 9A:
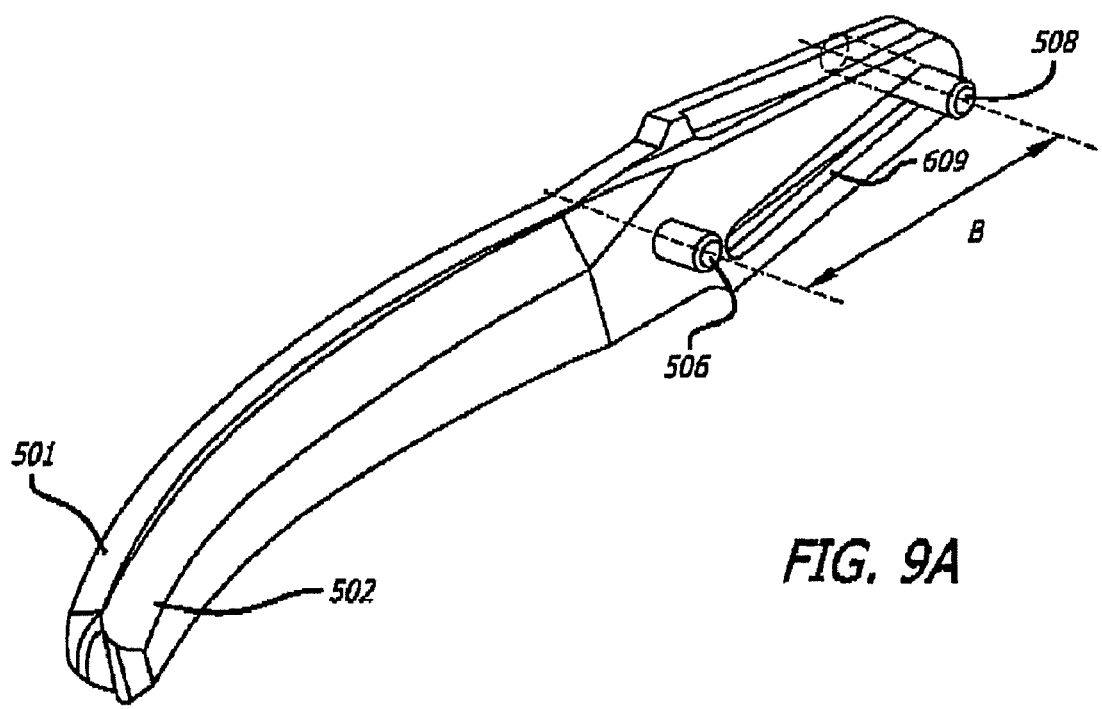
FIGS. 9A-9B illustrate the motion of the end effector assembly for the replaceable end effector cartridge illustrated in FIGS. 5A-8B.
Figure 9B:
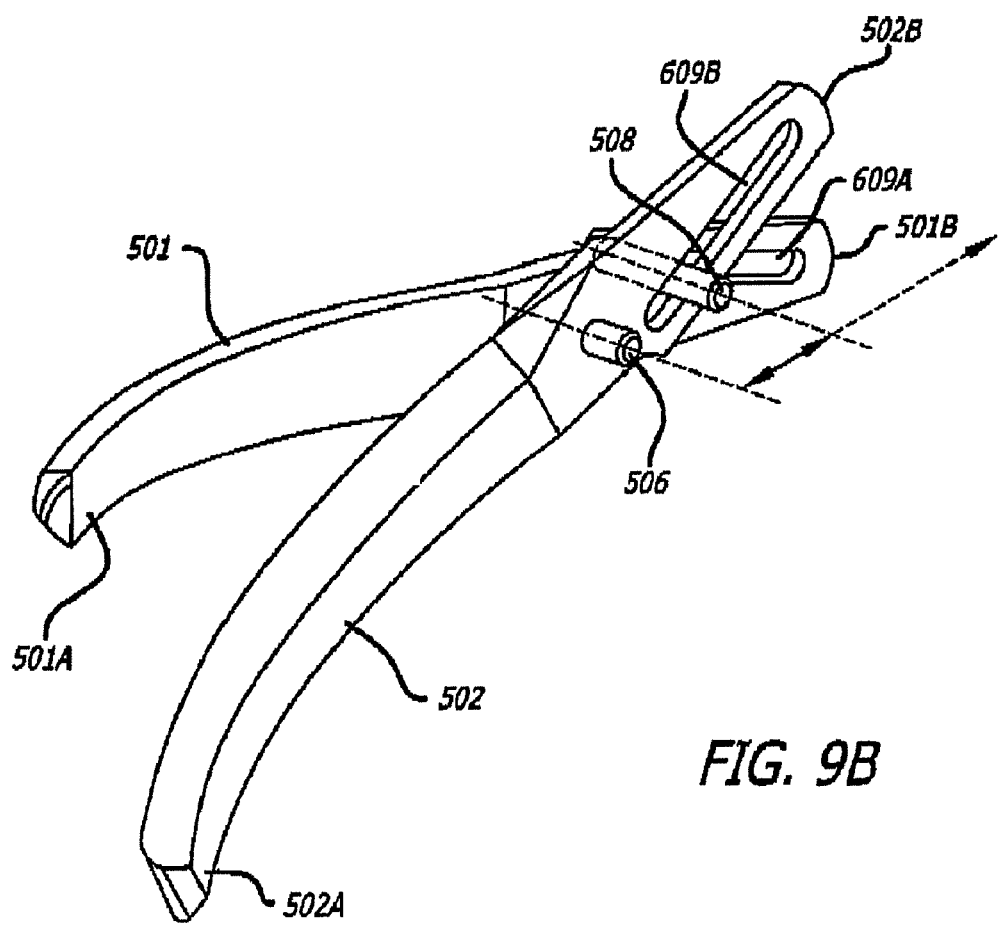

Referring now FIGS. 9A-9B, each end effector or blade 501, 502 has a corresponding generally longitudinal cam slot 609A,609B respectively in the base portion 501B,502B of each end effector. The cam slots 609A,609B are at the opposite end from distal shear portions 501A and 502A. The drive pin 508 passes through both of the cam slots 609A,609B and has an axis generally parallel and proximal to the pivot screw 506. The slots 609A,609B are angularly offset from the pivot screw 506, so that the line extensions of the slots do not pass through pivot screw 506. The drive pin 508 slides longitudinally with respect to the pivot screw 506 as illustrated by the arrow B. As the drive pin 508 slides longitudinally along the cam slots 609A,609B in a crossed cam-slot engagement, the blades are caused to rotate about the pivot screw. As the drive pin 508 slides proximally, the blades close upon one another in a shearing action as shown in FIG. 9A. As the drive pin slides distally, the blades open apart from one another, as shown in FIG. 9B.

The end effectors or blades 501,502 preferably comprise conductive materials, such as stainless steel and the like, so as to provide a conduction path to tissue. The end effectors or blades 501 and 502 may be straight or curved at the shearing surfaces thereof (e.g., curved Metzenbaum blades).

Referring now back to FIG. 6B, a cable of cable loop 650B is coupled to the pulley 601B. The cable of the cable loop 650B is routed between the wrist and the tool base over slanted idle pulleys 651A-651B that are slanted with a centerline of the wrist and idle pulleys 651C-651D that are in alignment thereto. FIG. 6B also illustrates the wire 448 routing between the receptacle 404 and the tool base over the idle pulley 651E. The idle pulleys are non-driven pulleys. The cable of the cable loop 650B may be pulled in one direction to close the jaws or blades of the end effector. The cable of the cable loop 650B may be pulled in an opposite direction to close the jaws or blades of the end effector.

Referring to FIG. 6A, the wristed receptacle 404 further includes the inner connector liner 610 at a distal portion of the cylinder 602. The pivot bolt 506 engages the connector liner 610 at the distal portion of the cylinder by means of an "L" shaped slot 616. The catch 517 of the spring latch 507 engages the recess 617 in the inner connector liner 610. A tab 619 of the inner connector liner 610 at the recess 617 couples to the catch 517 to form an electrical connection between the liner 610 and the cartridge 414.

In one embodiment of the invention, the robotic electrosurgical tool is monopolar with one or both end-effectors 501-502 being electrically hot with the same polarity. In this case, the patient is grounded in order to complete the circuit.

In another embodiment of the invention, the robotic electrosurgical tool may be bipolar with both end-effectors 501-502 being electrically hot with differing polarity. That is, each end-effector may be wired independently to be hot such that when the same tissue is touched by each, the circuit is completed. In which case, the end effectors 501-502 may be electrically isolated from each other. Two insulated conductive wires 448 are routed from the tool base through the shaft and the wrist. One wire couples to the end effector 501. The other wire couples to the end effector 502.

The insulated conductive wire 448 is routed from the tool base through the shaft and the wrist to the wristed receptacle 404. The insulated conductive wire 448 is crimped and electrically coupled to the inner connector liner 610 by a crimp tab 611. In other cases, the wire may be welded or soldered to the inner connector liner 610. In this manner the inner connector liner 610 can be energized. The latch 507, screw 506, and end effectors 501-502 may be formed out of a metal, alloy, or metallized material to be conductive. When the cartridge is coupled into the receptacle, the latch 507 and screw 506 may mechanically and electrically couple to the inner connector liner 610. That is, when the cartridge 414 is coupled into the receptacle 404, its conductive components become electrically alive. As the end effectors are conductive and rotatably coupled to the latch 507 and screw 506, the end effectors 501-502 can be energized by a current flowing through the insulated conductive wire 448 from the tool base. That is, the wire 448 supplies electrical power from an electrical generator to the end effectors.

A number of components of the receptacle 404 are nonconductive or insulative to avoid shorting the current in the insulated conductive wire 448 to an undesired location in a surgical site or back to the wrist 402. The piston 604 and the cylinder 602, for example, may be formed of an insulative material such as plastic (e.g., polypropylene, or flouropolymer). The connecting rod 606, piston pin 607 and crank pin 657 may also be formed of an insulative material such as plastic. However, in a preferred embodiment of the invention, the connecting rod 606, piston pin 607 and crank pin 657 are formed of a metal or a metal alloy for the strength of the material to withstand applied forces. The components that are formed of insulative materials, such as plastic, are not electrically alive. The wrist 402, shaft 416, and tool base are preferably not alive as they are electrically isolated through the insulative components. However, the inner connector liner 610 is conductive to make electrical contact and may be the one "live" part of the cylinder and receptacle.

The wristed receptacle 404 may further include an insulating sleeve 612 over the cylinder 602 and/or an o-ring seal 614 within the cylinder 602 to avoid contamination and shorting when the insulated conductive wire 448 is energized. The wrist 402 may be isolated externally by the insulating sleeve. The insulating sleeve 612 may be formed of silicone insulation disposed over an outer surface of the cylinder 602 in one embodiment of the invention. The wrist 402 may be isolated internally by one or more o-ring seals 614 within the cylinder 602. The o-ring seal 614 may be fitted into a slot 624 around the outer surface of the piston 604. The o-ring seal deters liquid from forming a conductive path between the inner connector liner 610 and the wrist 402 and shorting current to ground thereby. Additionally, the o-ring seal 614 deters contaminants from reaching the wrist 402 through the receptacle 404.

Figure 7A:
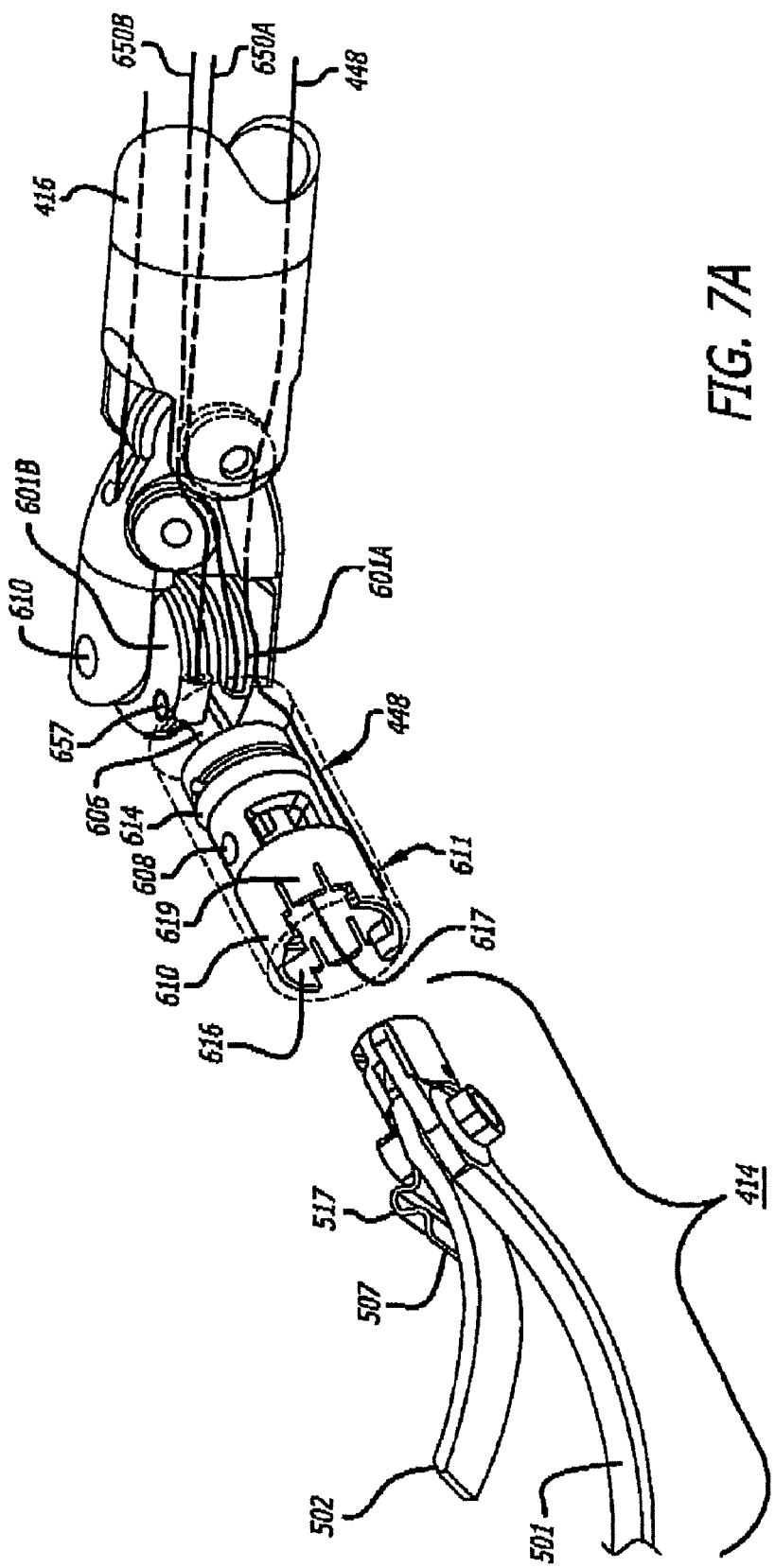
FIGS. 7A-7B illustrate cutaway exploded views of the replaceable end effector cartridge and the robotic surgical tool.
Figure 7B:
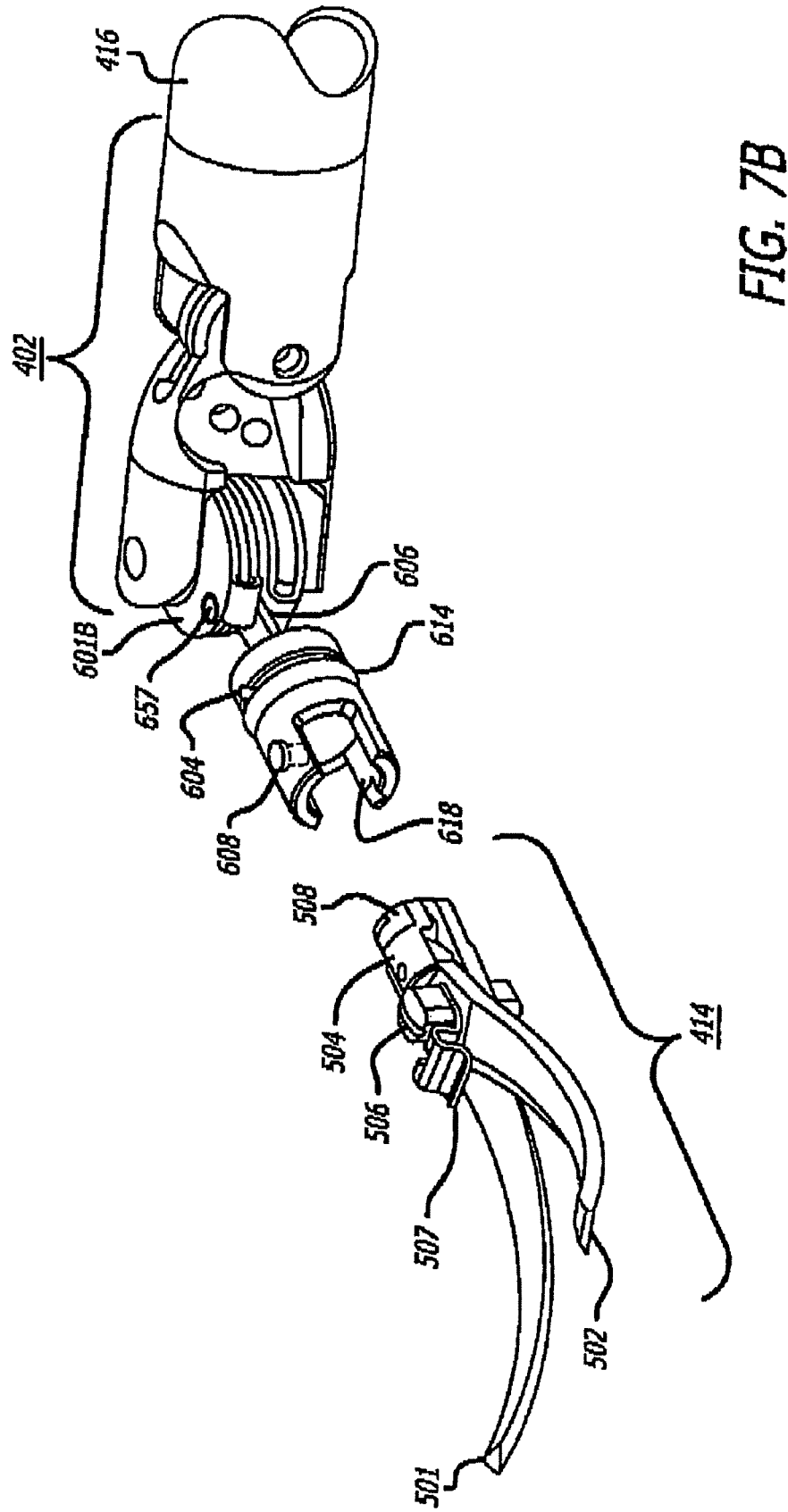

Referring now to FIGS. 7A-7B, perspective cutaway views of the wrist 402, the receptacle, and the replaceable end-effector cartridge 414 decoupled from the receptacle are illustrated. FIGS. 7A-7B better illustrate the piston 604, the inner connector sleeve 610, and how the connecting rod 606 couples to the pulley 601B through the crank pin 657. The crank pin 657 is off center of the pulley 601B so that as it rotates it can linearly moves the piston 604. FIG. 7A better illustrates how cables of the cable loops 650A-650B are routed through the shaft 416 from the tool base to the respectively pulleys 601A-601B in the wrist 402. FIG. 7A also better illustrates how the wire 448 is routed from the tool base through the shaft 416 and the wrist 402 to the receptacle 404. FIG. 7B better illustrates the L-shaped slot 508 in the sleeve 504 of the cartridge 414.

One cable loop 650B is used to open and close the jaws/blades of the end effectors 501-502. Two cable loops need not be used to open and close a pair of end effectors. This provides a greater degree of freedom of movement. Cable loop 650A may be used to yaw the receptacle (e.g., move left or right).

Referring now to FIGS. 8A-8B, the yaw or rotation of the receptacle 404 and the cartridge 414 is now illustrated. Cable loop 650A coupled to pulley 601A is used to yaw (e.g., move left and right or up and down) the receptacle 404 (including any cartridge mounted therein) about a wrist pin 640. Cable loop 650A is also routed over idle pulleys 651A-651B in the wrist 402 to the pulley 601A. A cable loop 648 may be routed from a spool through the shaft to a drive pulley in the wrist 402 in order to control the pitch of the wrist.

The insulating sleeve 612 may be formed of an insulative material disposed over an outer surface of the cylinder 602 in one embodiment of the invention. The insulating sleeve 612 helps to electrically isolate the wrist 402 from the end-effectors 501-502. In one embodiment of the invention, the insulating sleeve 612 is formed by using a fluoropolymer heat shrink over the cylinder. In another embodiment of the invention, the insulating sleeve 612 is formed by using a silicon overmold disposed over a plastic cylinder. In yet another embodiment of the invention, the insulating sleeve 612 is formed out of plastic such as polypropylene or fluoropolymer.

While the end effector cartridge has been described as being replaceable, in another embodiment of the invention the end effectors are not a replaceable cartridge but instead are a part of the receptacle that includes the end effectors and its cam mechanism. In this manner, the spring latch 507, the recess 617, L-shaped slot 508, and drive pin 608 need not be provided. Manufacturing costs may be lowered in this case due to the standard components that can be used, such as the interface base, the shaft, and the wrist for the manufacture of the robotic tool.

Replaceable End Effector Cartridge for Cam Driver Actuator

In the embodiments of the replaceable end effector cartridge previously described, the end effectors were actuated by a piston applying a force substantially in line or parallel with the length of the cartridge. In the embodiments of the replaceable end effector cartridge described below, the end effectors are actuated by a force that is applied substantially perpendicular to the length of the cartridge.

Figure 10A:
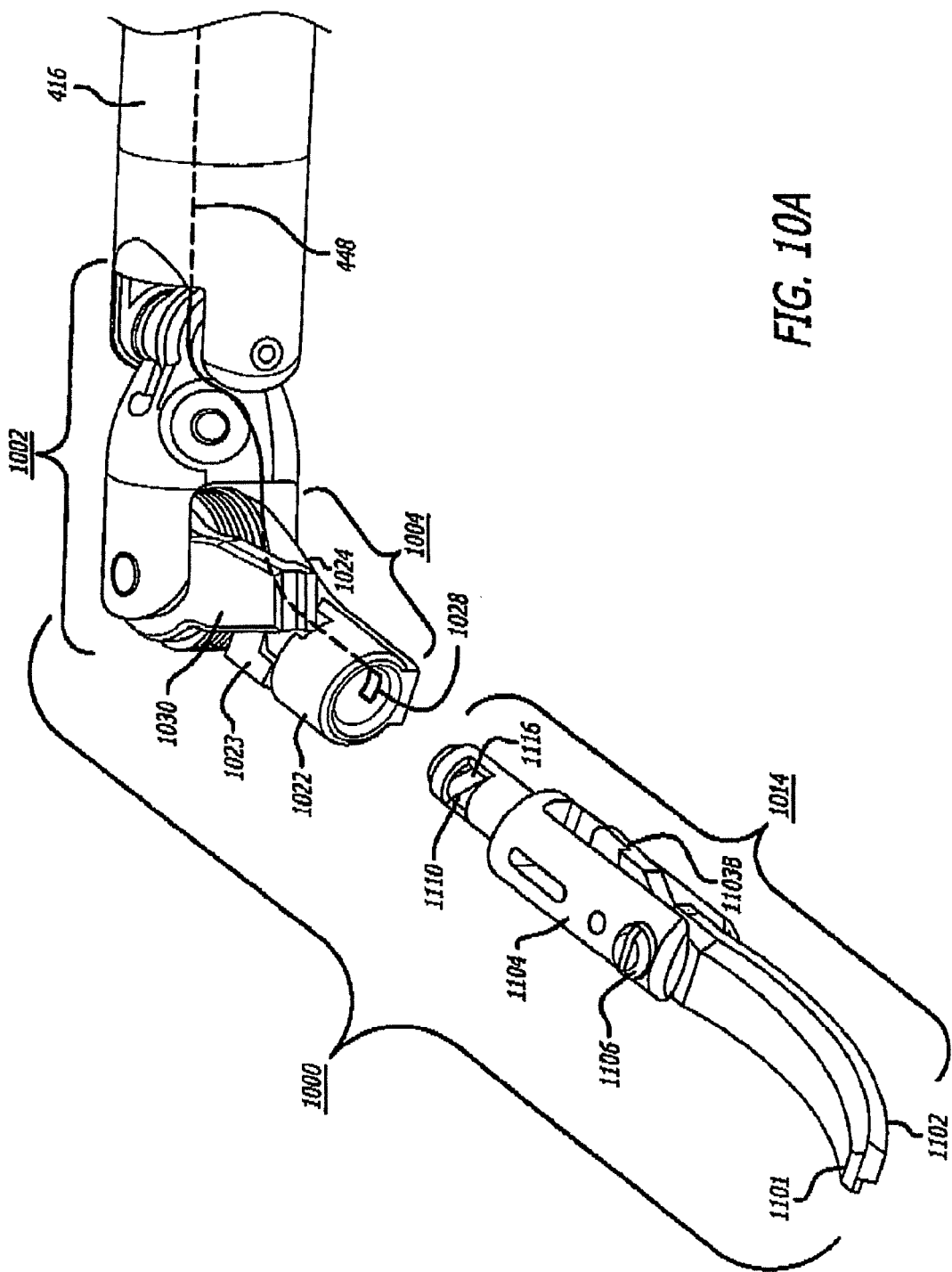

Referring now to FIG. 10A, a robotic electro-surgical tool 1000 is illustrated including a replaceable end effector cartridge 1014 to couple into a receptacle 1004 coupled to a mechanical wrist 1002 at the distal end of the shaft 416. The interface base 412 with its electrical connector 474 is the same for the robotic electro-surgical tool 1000 as is illustrated in FIGS. 4A-4E. The replaceable end effector cartridge 1014 is actuated differently than the replaceable end effector cartridge 414.

Figure 11:
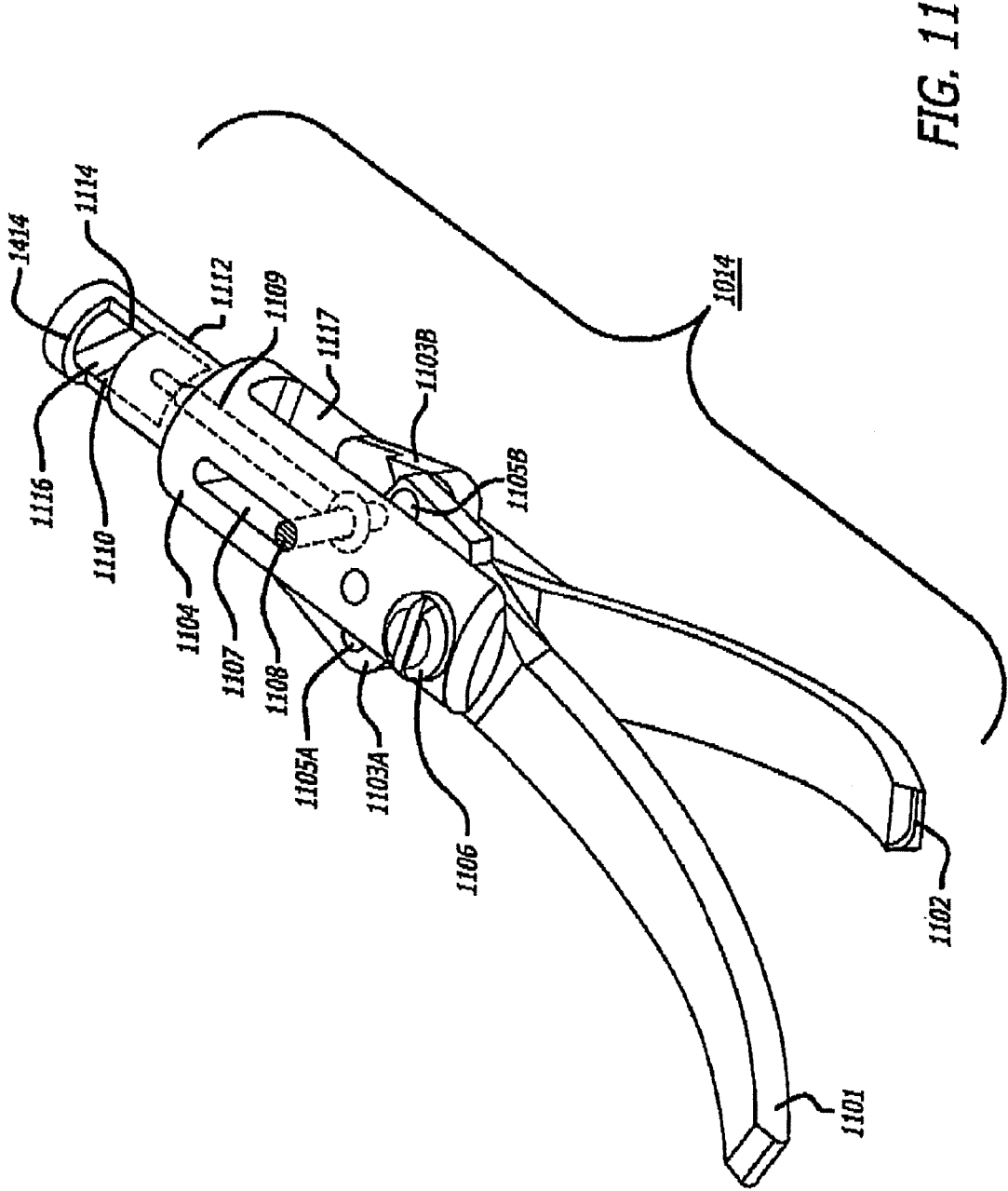
FIG. 11 illustrates a magnified top perspective view of the replaceable end effector cartridge of FIG. 10A-10D.

Referring now to FIGS. 10A and 11, the replaceable end effector cartridge 1014 may include one fixed and one moveable or two moveable end effectors 1101-1102, one or two links 1103A-1103B, a clevis or U-shaped housing 1104, one or two link pins 1105A-1105B, a pivot screw 1106, a drive pin 1108, a rod 1109 (see also FIG. 14), and a driver accessory 1110 coupled together as shown. In a preferred embodiment of the invention, there are two moveable end effectors 1101-1102, each of which is a blade of a scissors or shear. The clevis 1104 looks like a tuning fork having a hollow cylindrical base coupled to a U-shaped metal piece with holes in each side through which a screw, bolt, pin, or rivet may run from each side.

The driver accessory 1110 is coupled to one end of the rod 1109 to push on the linkage to open the end effectors 1101-1102 and to pull on the linkage to close the end effectors 1101-1102. An opposite end of the rod 1109 is coupled to the drive pin 1108 as are one end of the links 1103A-1103B. Through the rod 1109 and drive pin 1108, the driver accessory 1101 can push and pull on the links 1103A-1103B. The links 1103A-1103B are respectively coupled at an opposite end to a base region of the end effectors 1102 and 1101 through the link pins 1105A-1105B, respectively. A force applied on the links 1103A-1103B can cause the end effectors 1101-1102 to pivotally open and close around the pivot screw 1106.

Figure 12B:
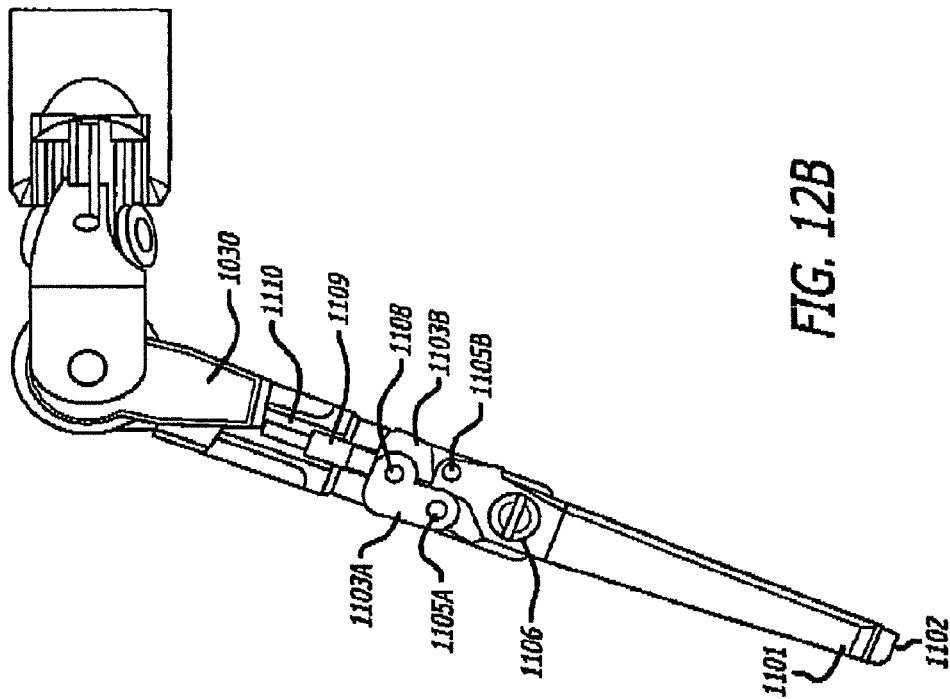
FIGS. 12B and 13B illustrates top cutaway views of the replaceable end effector cartridge of the second embodiment mounted to the robotic surgical tool of FIGS. 10A-10D in a closed and open actuated position, respectively.
Figure 12A:
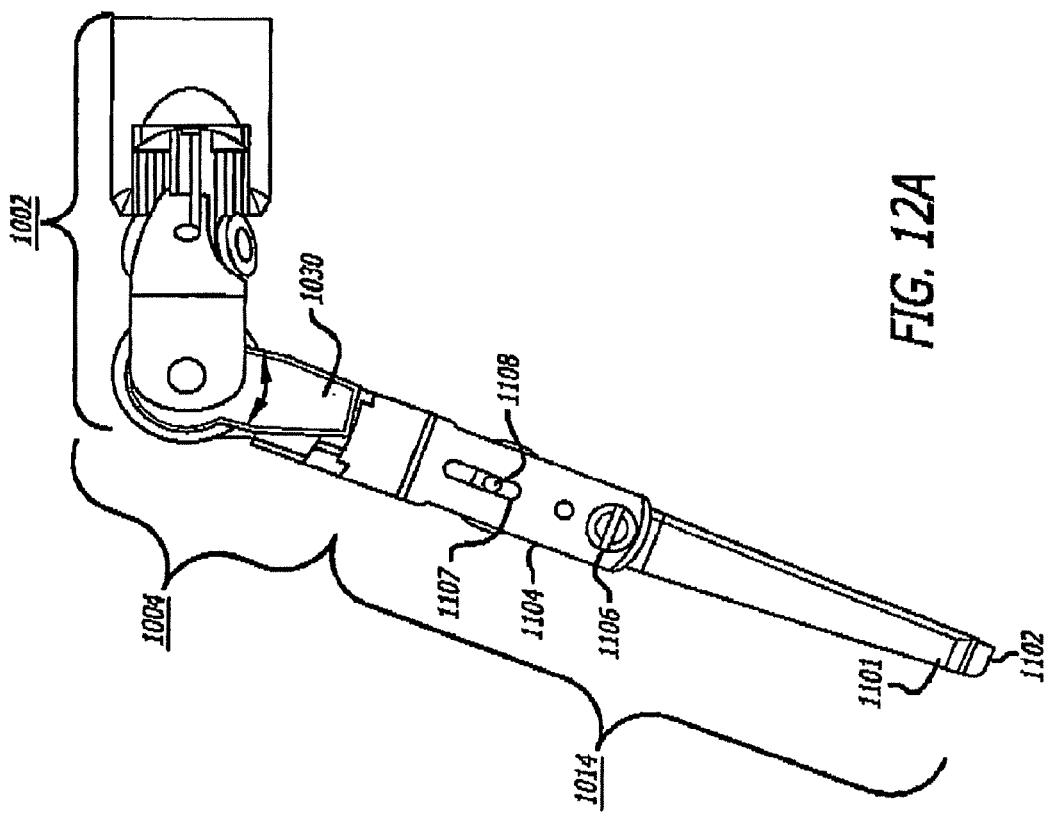
FIGS. 12A and 13A illustrates top views of the replaceable end effector cartridge of the second embodiment mounted to the robotic surgical tool of FIGS. 10A-10D in a closed and open actuated position, respectively.
Figure 13B:
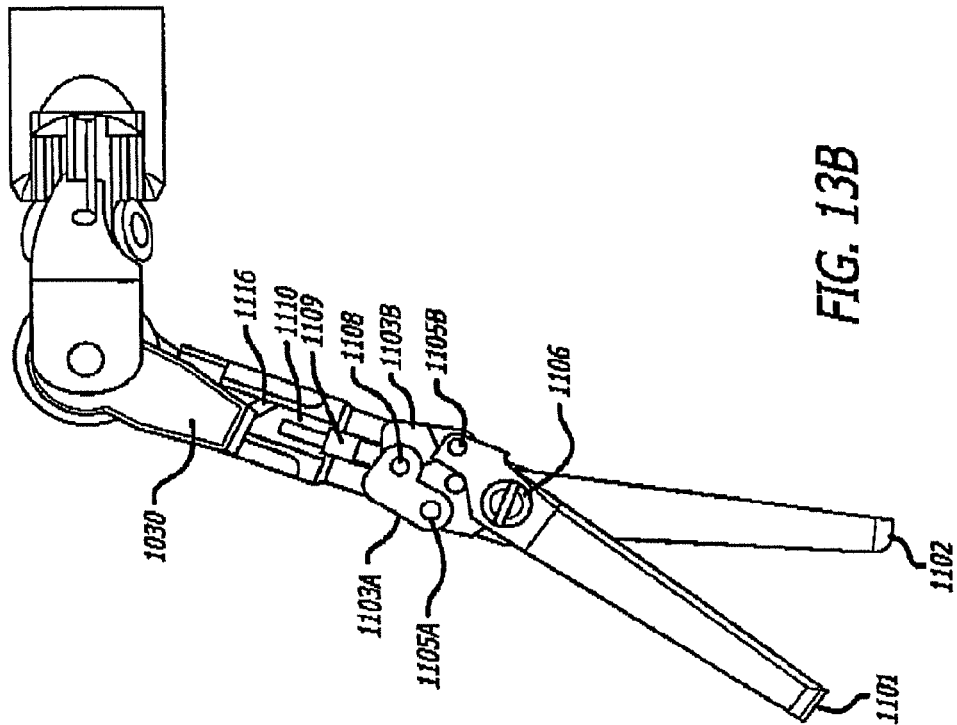
Figure 13A:
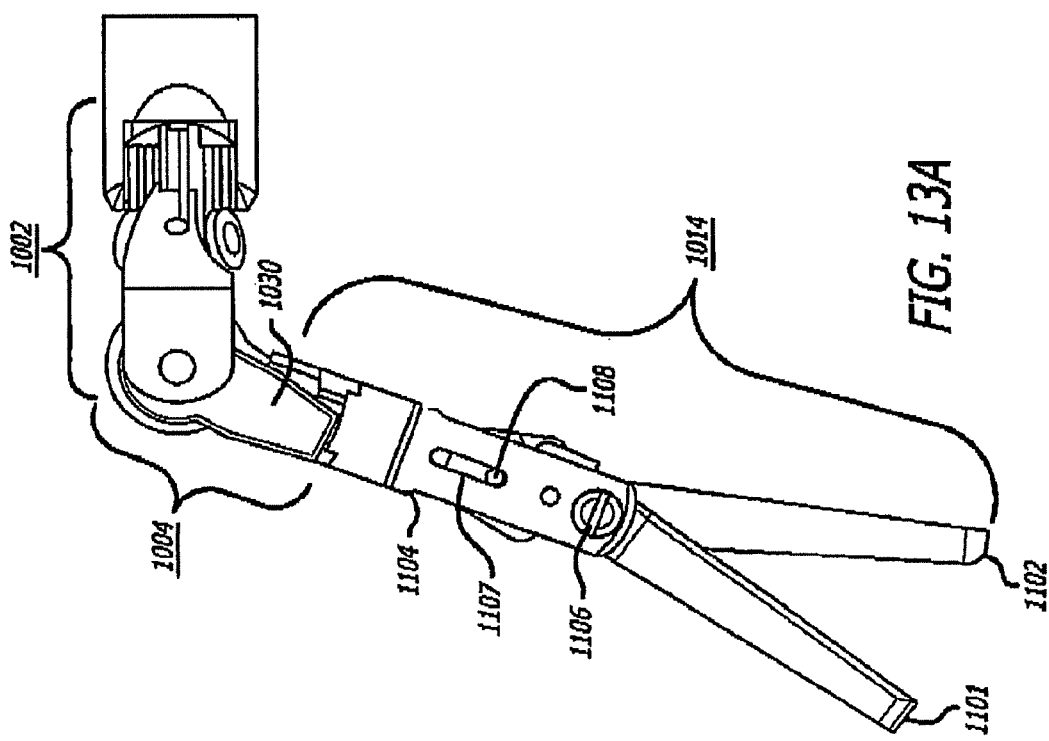

FIGS. 12A-12B illustrates the position of the driver accessory 1110, the rod 1109, the drive pin 1108, and the links 1103A-1103B to pivot close the end effectors 1101-1102 around the pivot screw 1106. FIGS. 13A-13B illustrates the position of the driver accessory 1110, the rod 1109, the drive pin 1108, and the links 1103A-1103B to pivot open the end effectors 1101-1102 around the pivot screw 1106.

Referring back to FIG. 11, the clevis 1104 includes a slot 1117 in which the links 1103A-1103B, the rod 1109, and the base portions of the end effectors 1101-1102 may slide and/or rotate. The clevis 1104 further includes a slot 1107 in which the drive pin 1108 may linearly travel to move the links 1103A-1103B and open and close the end effectors 1101-1102. A base portion 1112 of the clevis 1104 includes a drive opening 1114 that provides access to a cam slot 1116 of the driver accessory 1110. The cam slot 1116 is formed at an angle other than ninety degrees, or a multiple thereof, so that the drive accessory 1110 can be linearly moved within the base portion 1112 of the clevis 1104 by a dog 1032 of a driver moving perpendicularly with the longitudinal axis (see FIG. 16 for an illustration of the dog 1032).

Figure 14:
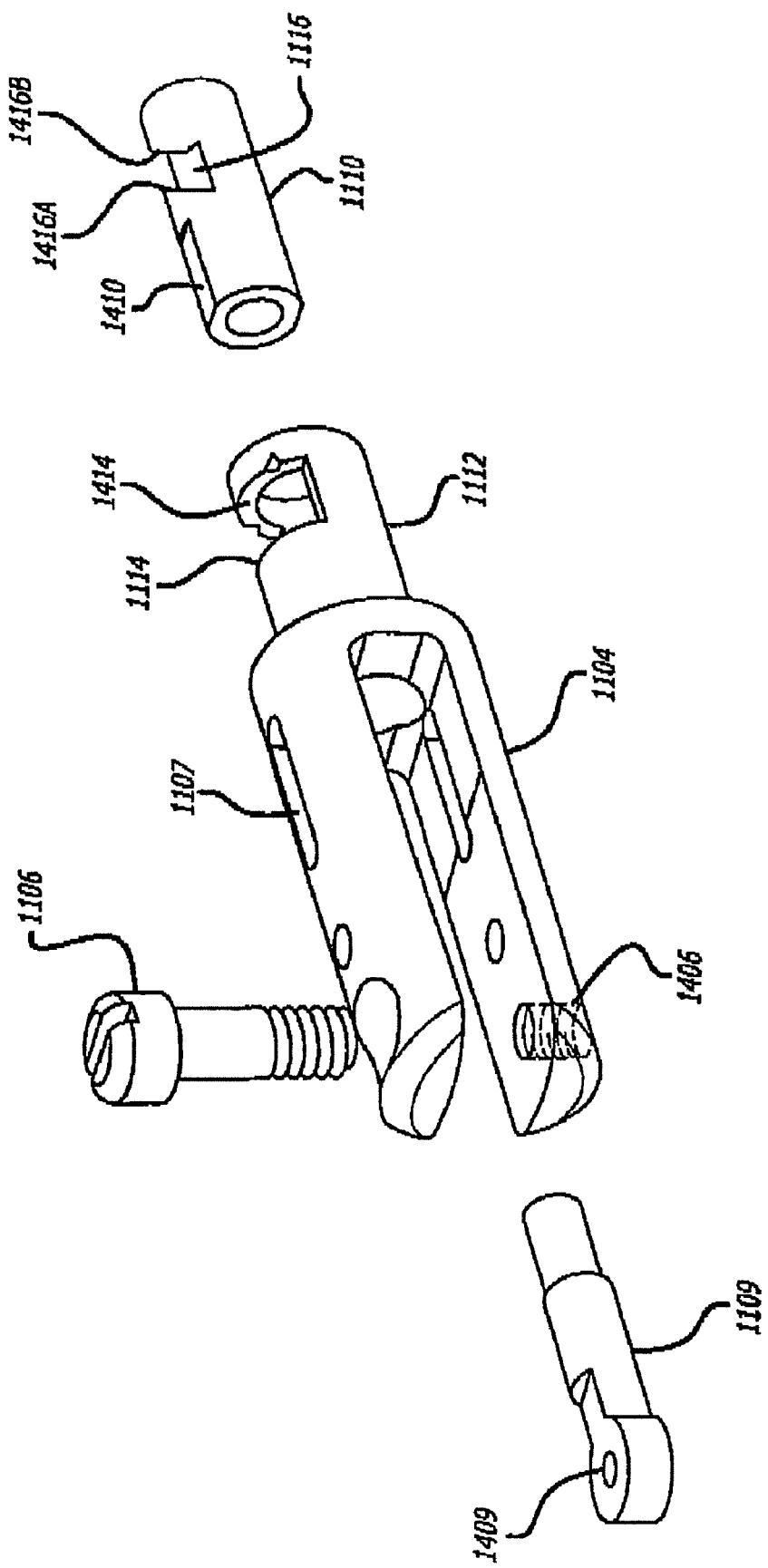
FIG. 14 illustrates a magnified side exploded view of some of the elements of the replaceable end effector cartridge of FIG. 11.

Referring now to FIG. 14, an exploded view of cartridge 1014 is illustrated without the linkage 1103A-1103B, the pins 1103A-1103B and 1108, and the end effectors 1101-1102. FIG. 14 provides a perspective view of the drive accessory 1110 and the rod 1109. The drive pin may be press fit into an opening 1409 in one end of the rod 1109. The pivot screw 1106 may be threaded into a screw hole 1406 of the clevis 1104.

The drive accessory 1110 slides linearly within the base portion 1112 of the clevis 1104 without rotating from the force applied by the driver. The driver accessory 1110 and the inner portion of the base portion 1112 of the clevis may be shaped so that drive accessory does not rotate. A flat area 1410 on the driver accessory 1110, for example, may mate with a flat area in the inner portion of the base 1112 so that the driver accessory 1110 does not rotate, but instead, slides linearly.

The cam slot 1116 of the driver accessory 1110 includes a first camming surface 1416A on one side and a second camming surface 1416B on the opposite side of the slot. The first camming surface 1416A is used to push forward on the driver accessory 1110, the rod 1109, and the drive pin 1108 to open the end effectors. The second camming surface 1416B is used to pull out on the driver accessory 1110, the rod 1109, and the drive pin 1108 to close the end effectors.

To hold the cartridge 1014 in place to the receptacle 1004, the base 1112 of the clevis 1104 includes a retention surface 1414 near the drive opening 1114. The retention surface 1414 is engaged by the driver of the receptacle 1004 as is discussed further below with reference to FIG. 10D.

A substantial number of components of the cartridge 1014 are formed out of metal, a metal alloy, or a metalized material to conduct electricity. In particular, the clevis 1104 is formed out a metal, a metal alloy or a metalized material to couple to the metal contact 1028 inside a sleeve 1022 of the receptacle 1004.

Toggle Wristed Receptacle with Cam Driver Actuator

Referring now back to FIG. 10A, the receptacle 1004 includes the sleeve 1022 coupled to a rotatable base 1024. One end of the rotatable base 1024 is rotatably coupled to the toggle wrist 1002. The sleeve 1022 includes an open portion 1023 to allow the driver 1030 of the toggle wrist 1002 to interface with the base 1112 of the cartridge 1004 and the drive accessory 1110.

The insulated wire 448 from the interface base is routed through the shaft 416 and the toggle wrist 1002 over the rotatable base 1024 and into the sleeve 1022 to couple to the metal contact 1024. But for the metal contact 1024, the receptacle 1004 (including the sleeve and the base) and the driver 1030 are formed out of an insulator, such as plastic. In contrast, substantially all the components of the cartridge 1014 are formed out of a conductor, such as metal, so that they are electrically live when the wire 448 is energized by a generator. The receptacle 1004 and the driver 1030 isolate the conductive components of the cartridge 1014 so that they are not electrically live when the wire 448 is energized.

Referring now to FIG. 10B, the driver 1030 includes a step 1033 with an angled tab or dog 1032 at a base surface. The angled tab or dog 1032 interfaces with the slot 1116 in the driver accessory 1110. A first camming surface 1036A and a second camming surface 1036B of the dog 1032 respectively interface with the camming surfaces 1416A-1416B of the slot 1116. The dog 1032 is on an angle and slides along the slot 1116 when the driver is rotated over and into the driver opening 1114. As the dog 1032 slides along the slot its camming surfaces 1036A-1036B push or pull on the camming surfaces 1416A-1416B of the slot to push in or pull out on the driver accessory 1110.

The step 1033 further provides a locking surface 1034 for the driver 1030 along a back portion thereof. The locking surface 1034 of the driver 1030 engages the retention surface 1414 of the base 1112 of the clevis 1104 to couple the cartridge 1014 to the receptacle 1004 and the surgical tool 1000.

Referring to FIGS. 10B-10C, the sleeve 1022 includes an open portion 1023 to allow the driver 1030 of the toggle wrist 1002 to interface with the base 1112 of the cartridge 1004 and the drive accessory 1110.

Referring to FIG. 10D, the locking surface 1034 of the driver 1030 is slidingly coupled to the retention surface 1414 of the base 1112 of the clevis 1104 in order to engage the retention feature. The front step 1033 of the driver also engages a lip 1023 of the sleeve 1022. This couples the cartridge 1014 to the receptacle 1004 and the surgical tool 1000 as the driver 1030 continues to rotate the locking surface 1034 within the drive opening. That is, the driver 1030 can rotate about the wrist pin 1040 over a range of angles and maintain the engagement of the retention feature.

Additionally, the dog 1032 of the driver 1030 is in the cam slot 1116 of the driver accessory 1010 of the cartridge 1014 to engage the camming mechanism. As the driver 1030 rotates, it slides the dog 1032 in the cam slot 1116 of the driver accessory 1010. This causes the camming surfaces to be engaged and push out or pull in on the driver accessory 1010. In one embodiment of the invention, as the driver 1030 rotates clockwise the driver accessory 1010 is pushed away from the wrist pin 1040 to open the end effectors; and as the driver 1032 rotates counter clockwise the driver accessory 1010 is pulled in towards the wrist pin 1040 to close the end effectors.

The toggle wrist 1002 includes a first pulley 1050 that is coupled to the driver 1030 to rotate it around a wrist pin 1040. The toggle wrist 1002 further includes a second pulley 1052 coupled to the base 1024 of the receptacle 1004 to yaw the receptacle and the cartridge about the wrist pin 1040.

Referring now to FIGS. 15-16, the toggle wrist 1002 may include a first joint 1560, a second joint 1562, idle pulley pairs 651A-651D idle pins 1551A-1551B, a first wrist pin 1540, a second wrist pin 1040, the driver 1030, pulleys 1050,1052; and the receptacle 1004 coupled together as shown in FIG. 10A. Further details of mechanical wrists that may be applicable to the toggle wrist 1002 are described in U.S. Pat. Nos. with filing dates and named inventor as follows U.S. Pat No. 5,792,135, May 16, 1997, Madhani et al; U.S. Pat No. 5,979,900, May 16, 1997, Madhani et al; U.S. Pat No. 5,807,377, May 16, 1997, Madhani et al; U.S. Pat No. 6,206,903, Oct. 8, 1999, Ramans; U.S. Pat No. 6,312,435, Wallace et al., Oct. 8, 1999; U.S. Pat No. 6,371,952, Jun. 28, 1999, Madhani et al; U.S. Pat No. 6,394,998, Sep. 17, 1999, Wallace et al.; U.S. Pat No. 6,676,684, Sep. 4, 2001, Morley et al.; U.S. Pat No. 6,685,698, Jan. 10, 2003, Morley et al.; U.S. Pat No. 6,699,235, Mar. 2, 2004, Wallace et al.; U.S. Pat No. 6,746,443, Jul. 27, 2000, Morley et al.; U.S. Pat No. 6,817,974, Jun. 28, 2002, Cooper et al.; and application Ser. No. 10/726,795, Pub. No.: US 2004/0138700 A1, Dec. 2, 2003, Cooper et al., all of which are incorporated herein by reference.

The pulleys 1050,1052 may each include a D-shaped opening 1650,1652 respectively. The driver 1030 includes a D-shaped insert 1550 that can couple into the D-shaped opening 1650 of the pulley 1050. In this manner, the pulley 1050 is coupled to the driver 1030 to hold and control the end effectors of the replaceable end effector cartridge 1014. The receptacle 1004 includes a D-shaped insert 1552 that can couple into the D-shaped opening 1652 of the pulley 1052. In this manner, the pulley 1052 is coupled to the receptacle 1004 so it and the cartridge 1014 can be yawed left and right or up and down.

In FIG. 16, a bottom view of the dog 1032 is illustrated. The dog 1032 is slanted on an angle with the radius of the driver 1030 to mate with the cam slot 1116 in the driver accessory 1110. The dog 1032 includes the camming surfaces 1036A-1036B.

Referring now back to FIGS. 12A-12B, operation of the driver 1030 is now described with the end effectors 1101-1102 in an initially closed position. The driver 1030 rotates to first lock the cartridge 1014 into the receptacle 1004 coupled to the mechanical wrist 1002 and the robotic surgical tool 1000. As previously discussed, the locking surface 1034 of the driver 1030 is slidingly coupled to the retention surface 1414 of the base 1112 of the clevis 1104 in order to engage the retention feature.

After locking the cartridge 1014 to the receptacle 1004, the driver 1030 is rotated further so that the dog 1032 mates with the slot 1116 of the driver accessory 1010 to begin to open the end effectors 1101-1102.

Referring now to FIGS. 13A-13B, further rotation in the driver causes the camming surfaces of the dog 1032 to mate with the camming surfaces of the slot 1116 in order to translate the rotating motion of the driver 1030 into a linear motion of the driver accessory 1010. From the camming mechanism, the driver accessory 1010 pushes on the rod 1109 and the driver pin 1108 to actuate the links 1103A-1103B to pivot and spread apart the end effectors 1101-1102 as illustrated. FIGS. 13A-13B illustrate a clockwise motion for the driver to open the end effectors. It is readily apparent that the camming mechanism can be designed to use a counter-clockwise rotation instead for the driver to open the end effectors.

To avoid the driver from losing the retention feature it may be limited in range to avoid the locking surface 1034 of the driver 1030 being disengaged with the retention surface 1414 of the base 1112 of the clevis 1104. The range of motion may be limited by the control system of the robotic surgical system or a mechanical mechanism may be used to avoid further rotation in the driver.

Once the end effectors 1101-1102 are pivoted open as illustrated in FIGS. 13A-13B, an opposite rotation in the driver 1030 can pivot closed the end effectors 1101-1102. The dog 1032 of the driver pulls back on the driver accessory 1010 which then pulls on the rod 1109 and the driver pin 1108 to actuate the links 1103A-1103B to pivot and pull closed the end effectors 1101-1102 to the position as illustrated in FIGS. 12A-12B. In one embodiment of the invention, the end effectors 1101-1102 are blades of a scissors or shears.

Generally, the cartridge design in the embodiments of the invention disclosed herein aims to keep the mechanical wrist dry. Current leakage from the instruments is minimized from areas other than the active electrode. For example, this may be accomplished by the outer tube design (e.g., materials, coatings), how the outer tube design relates to working with a metal cannula, hypotube segment lengths and locations, hypotube isolation, vectran isolation to "interrupt" a hypotube to contain current to the instrument front end (creates electrical discontinuity), a seal at the distal end of the instrument lumen to keep fluids out of the lumen, coatings on the boot, or materials on the boot. Boot durability may be maintained by material and coating selection. Additionally, scissor blades may be designed to minimize tissue sticking.

The embodiments of the invention are thus described. Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Additionally, while a mechanical wrist and various cam mechanisms and actuators are illustrated and described herein to actuate the end effectors, other types of mechanical wrists, as well as other cam mechanisms and actuators may be used to actuate the end effectors, such as the mechanical wrist, and cam mechanism and actuator illustrated by FIGS. 37-41 and described in U.S. Pat. No. 6,817,974, filed by Cooper et al. on Jun. 28, 2002 which has been incorporated by reference herein. Therefore, the above description should not be taken as limiting the scope of the invention which is defined by the appended claims.

What is claimed is:

1. A method comprising:
coupling a replaceable end effector cartridge to a receptacle of a robotic surgical tool;
translating a rotational motion into a linear motion; and
pivoting an end effector of the replaceable end effector cartridge in response to the linear motion;
wherein the translating includes
rotating a spool to pull on a cable routed in a shaft of the robotic surgical tool,
rotating a pulley in response to the pull on the cable,
reciprocating a rod rotatingly coupled to the pulley at a crank pin, and
sliding a piston in a cylinder of the receptacle in response to the reciprocating of the rod.

2. The method of claim 1, wherein
the pivoting includes
actuating a link coupled to the end effector in response to the linear motion.

3. The method of claim 1, further comprising:
engaging a retention feature to lock the cartridge to the receptacle.

4. The method of claim 1, further comprising:
energizing a generator to couple power to the replaceable end effector cartridge.

5. A method comprising:
coupling a replaceable end effector cartridge to a receptacle of a robotic surgical tool;
translating a rotational motion into a linear motion; and
pivoting an end effector of the replaceable end effector cartridge in response to the linear motion;
wherein the translating includes
rotating a spool to pull on a cable routed in a shaft of the robotic surgical tool,
rotating a pulley in response to the pull on the cable,
rotating a driver coupled to the pulley, the driver having a dog with camming surfaces, and
sliding a rod having a cam slot engaged with the camming surfaces of the dog in response to the rotation of the driver.

6. The method of claim 5, wherein
the pivoting includes
actuating a link coupled to the end effector in response to the linear motion.

7. The method of claim 5, further comprising:
engaging a retention feature to lock the cartridge to the receptacle.

8. The method of claim 5, further comprising:
energizing a generator to couple power to the replaceable end effector cartridge.

* * * * *